(12) United States Patent      (10) Patent No.:    US 12,611,308 B2
     Caiazza                        (45) Date of Patent:      Apr. 28, 2026

(54) MOLD WITH REMOVABLE INSERTS FOR FORMING A SPACER DEVICE FOR THE REPLACEMENT OF A JOINT PROSTHESIS

(71) Applicant: Tecres S.p.A., Sommacampagna (IT)

(72) Inventor: Emanuele Caiazza, Rome (IT)

( * ) Notice:  Subject to any disclaimer, the term of this patent is extended or adjusted under 35 U.S.C. 154(b) by 140 days.

(21) Appl. No.: 18/555,523

(22) PCT Filed: Apr. 16, 2022

(86) PCT No.: PCT/IB2022/053583
     § 371 (c)(1),
     (2) Date: Oct. 15, 2023

(87) PCT Pub. No.: WO2022/224114
     PCT Pub. Date: Oct. 27, 2022

(65)            Prior Publication Data
     US 2024/0033097 A1      Feb. 1, 2024

(30)        Foreign Application Priority Data

Apr. 19, 2021    (IT) ......................... 102021000009899

(51) Int. Cl.
     *A61F 2/30*            (2006.01)
(52) U.S. Cl.
     CPC .. *A61F 2/30942* (2013.01); *A61F 2002/3069* (2013.01); *A61F 2002/30957* (2013.01)
(58) Field of Classification Search
     CPC .................... A01F 2/30; A61F 2/30942; A61F 2002/30957; A61F 2002/3069; A61F 2310/00353; B29C 45/00; B29C 39/26; B29C 45/0046; B29C 45/0001; B29L 2031/7532; B32B 2274/00
See application file for complete search history.

(56)            References Cited

U.S. PATENT DOCUMENTS

| | | | | |
|---|---|---|---|---|
| 5,577,779 | A | * | 11/1996 | Dangel ................... E05C 19/06 |
| | | | | 220/326 |
| 5,887,751 | A | * | 3/1999 | Kroscher .............. A47J 45/071 |
| | | | | 220/573.1 |
| 8,920,152 | B2 | | 12/2014 | Hawkins |
| 9,433,506 | B2 | * | 9/2016 | Lomicka ................... A61F 2/38 |
| 2009/0157189 | A1 | | 6/2009 | Hartman |
| 2009/0175978 | A1 | * | 7/2009 | Hawkins .................. A61F 2/36 |
| | | | | 425/470 |
| 2016/0332328 | A1 | * | 11/2016 | Wüst ..................... A61F 2/3094 |
| 2018/0319057 | A1 | * | 11/2018 | Foroni ................... B29C 39/26 |

FOREIGN PATENT DOCUMENTS

| | | |
|---|---|---|
| EP | 2526900 | 11/2012 |
| WO | 2016071939 | 5/2016 |

* cited by examiner

*Primary Examiner* — Alison L Hindenlang
*Assistant Examiner* — Shibin Liang
(74) *Attorney, Agent, or Firm* — Themis Law

(57)            ABSTRACT

A mold for forming a spacer device for the replacement of a joint prosthesis. In particular, a mold that has at least two removable inserts.

33 Claims, 17 Drawing Sheets

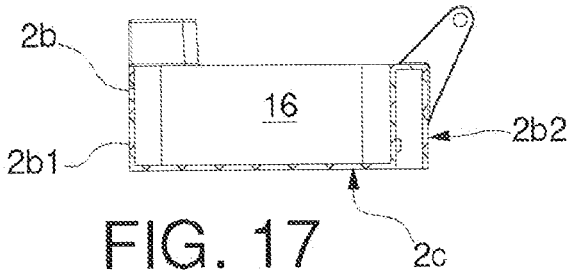
FIG. 17
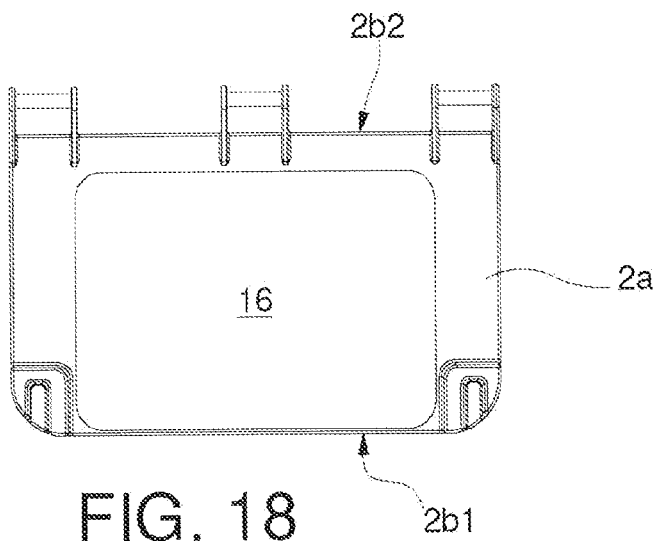
FIG. 18
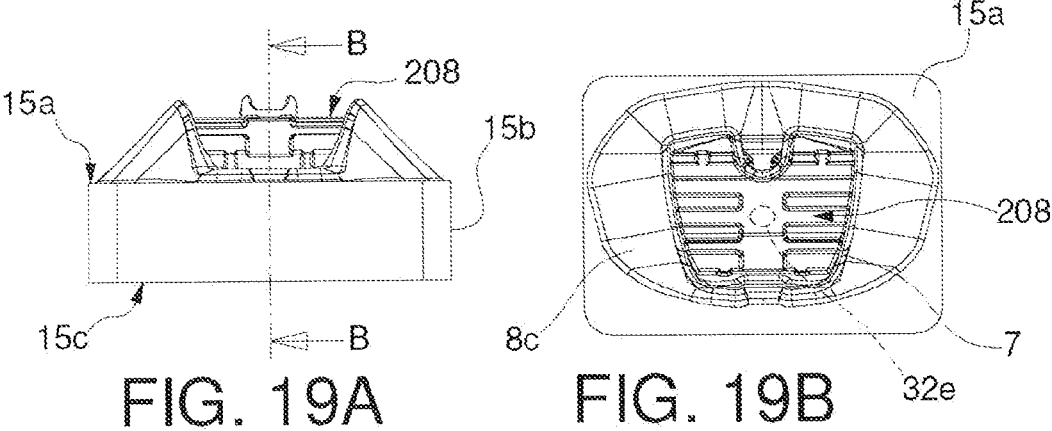
FIG. 19A          FIG. 19B

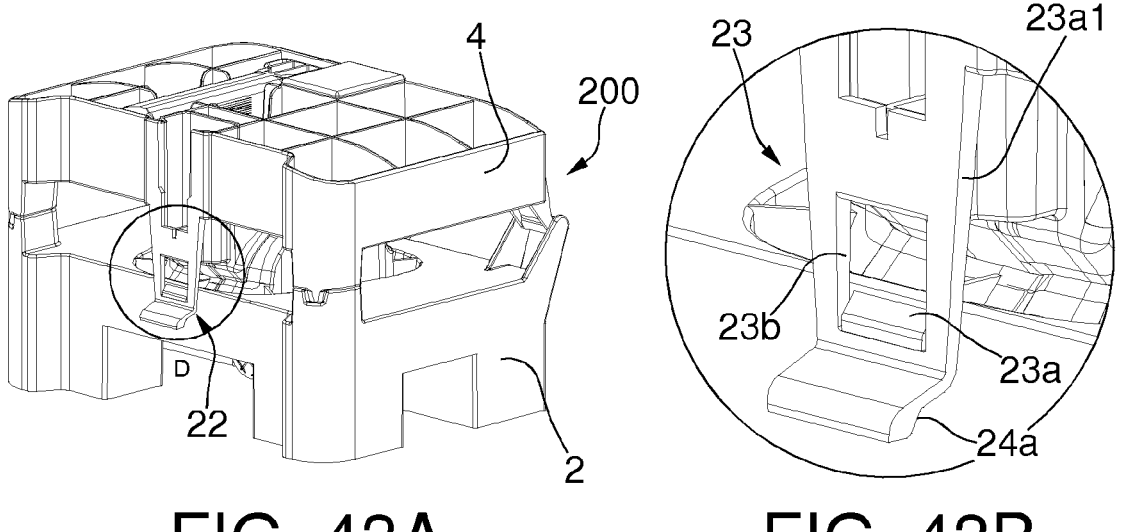
FIG. 43A        FIG. 43B
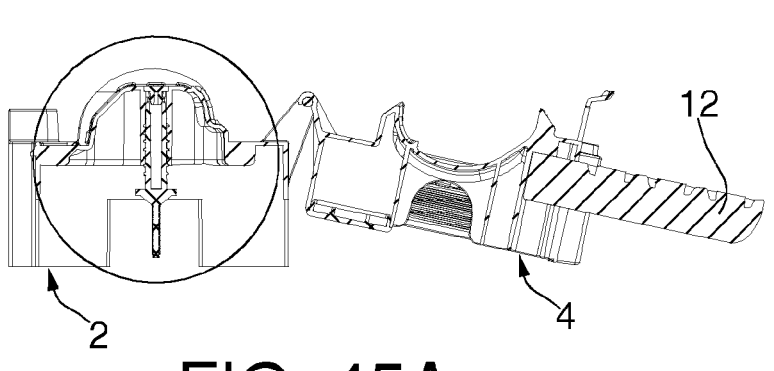
FIG. 45A
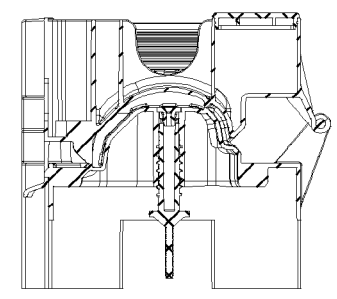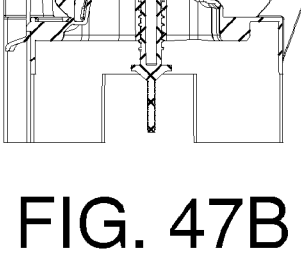
FIG. 47B
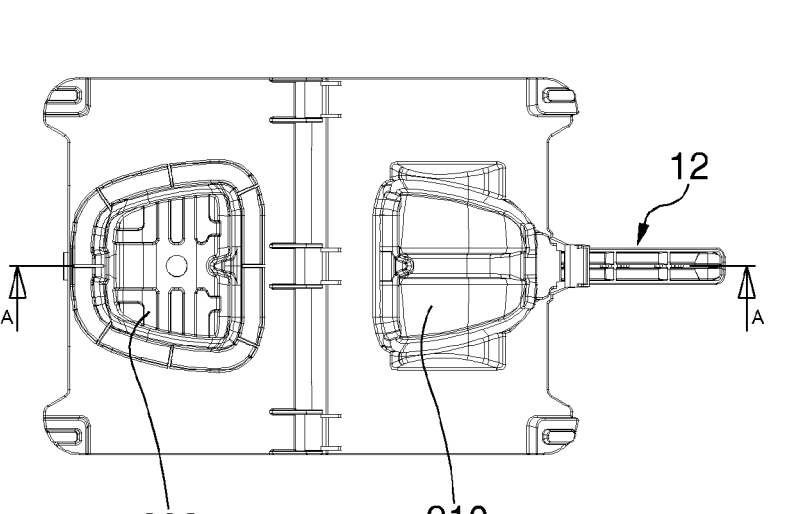
FIG. 44
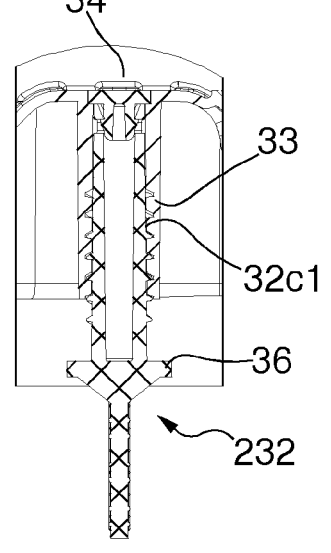
FIG. 45B

MOLD WITH REMOVABLE INSERTS FOR FORMING A SPACER DEVICE FOR THE REPLACEMENT OF A JOINT PROSTHESIS

TECHNICAL FIELD OF THE INVENTION

The present invention relates to a mold for forming a spacer device for the replacement of a joint prosthesis. In particular, the mold according to the present invention comprises at least two removable inserts.

STATE OF THE ART

The material with which the spacer devices for the replacement of a joint prosthesis are usually made is a material known, for example, as bone cement, which initially appears in a fluid state and hardens after a certain period of time. Once hardened, such material constitutes the structure of the spacer device.

The forming of the spacer device itself thus takes place through special molds which can be used directly by the surgeon in the operating theatre or also at external manufacturing sites which are then responsible for providing the surgeon, who has to perform the implant, with a preformed and substantially ready-to-use spacer device.

In the first case, doctors often use flexible molds which they fill with bone cement in a fluid state and from which, following solidification of the bone cement, they extract the formed spacer device by elastic or non-elastic deformation of the material making up the mold.

Because of the deformability of the material that constitutes the mold, however, the resulting spacer devices may not have the desired configuration or may have defects that, before implantation in the surgical site, must be eliminated by further processing, for example by smoothing, and the like.

There are other types of mold, made of rigid material, which make possible the formation of spacer devices of the desired configuration. However, it is often difficult to extract the spacers from these molds after the bone cement has hardened.

In addition, for reasons linked to the costs or to the warehouse storage, often such molds are made in a single size, or in few sizes, and they are needed to adapt to all the possible dimensional and anatomical variations of the patient who has to undergo the implant of the spacer device. Obviously, such determines a drawback, because the surgeon has to adapt such joint device to the real anatomical situation of the patient during, actually lengthening the time of the same and not obtaining in any case a result perfectly adherent to the real needs.

The U.S. Pat. No. 9,433,506 B2 discloses a mould for making an orthopaedic implant, for example a tibial component or a femoral component, comprising a first external component, a second external component and a block inside the two external components.

There is therefore a need for a new type of mold for forming a spacer device for the replacement of a joint prosthesis that overcomes the drawbacks of the prior art and that allows to adapt in an optimal way to the anatomical and dimensional situation of the patient who has to be implanted.

PURPOSES OF THE INVENTION

The main purpose of the present invention is thus to improve the state of the art in the field of molds for forming spacer devices for the replacement of a joint prosthesis.

Another purpose of the present invention is to provide a mold for forming a spacer device that is modular and that allows to meet the real anatomical and dimensional needs of the patient.

Another purpose of the present invention is to provide a mold for forming a spacer device that is quick and easy to use.

A further purpose of the present invention is to provide a mold for forming a spacer device that allows molding of the device in question by means of a substantially single operating step, without the need to perform further processing or finishing steps on the device obtained by means of the same.

Yet another purpose of the present invention is to provide a mold for forming a spacer device that can be manufactured at a competitive price.

A still further purpose of the present invention is to provide a mold for forming a spacer device that allows the doctor to choose the most suitable material for forming the mold itself, for example, an antibiotic mixture calibrated to the real needs of the patient and prepared, for example, on the instructions of a pharmacologist, based on the latter's identification of the specific patient's pathogenic flora.

A further purpose of the present invention is to provide a mold for forming a spacer device that is provided with an alternative configuration with respect to the state of the art.

According to an aspect of the present invention, a mold is provided for forming a spacer device for the replacement of a joint prosthesis as disclosed and claimed herein.

According to an aspect of the present invention, a method is provided for forming a spacer device for the replacement of a joint prosthesis also as disclosed and claimed herein.

According to a further aspect of the present invention a kit for a mold is for forming a spacer device for the replacement of a joint prosthesis is provided as further disclosed and claimed herein.

The dependent claims refer to preferred and advantageous embodiments of the invention.

BRIEF DESCRIPTION OF THE DRAWINGS

Further features and advantages of the present invention will become more evident from the detailed disclosure of some preferred exemplary embodiments of a mold for forming a spacer device, illustrated by way of example only, in the appended drawings, wherein:

FIG. 17 illustrates a sectional view taken along the plane A-A of the component of FIG. 16;

FIG. 18 illustrates a top view of the component of FIG. 16;

FIG. 19A illustrates a side view from of the insert of FIG. 15;

FIG. 19B illustrates a top view of the insert of FIG. 15;

FIG. 43A illustrates a perspective view of another version of a mold for forming a femoral spacer device for the knee, in a closed configuration, FIG. 43B illustrates an enlarged detail of FIG. 43A, FIG. 44 shows a plan view of the mold of FIG. 43A in an open configuration, FIG. 45A illustrates a sectional view taken along the plane of trace A-A of FIG. 44, FIG. 45B shows an enlarged detail of FIG. 45A, FIGS. 46A and 46B illustrate plan views of the mold of FIG. 43A, FIG. 47B illustrates a sectional view taken along the plane of trace C-C of FIG. 47A.

In the accompanying drawings, identical parts or components are identified by the same numerals.

EMBODIMENTS OF THE INVENTION

The present invention relates to a mold for forming a spacer device for replacing a joint prosthesis.

As it is usual, the spacer device is a temporary, disposable device which is implanted in the human body, for example at a joint in the human body, to replace a permanent joint prosthesis. This occurs basically because the implant site of the permanent joint prosthesis is infected and it becomes necessary, on the one hand, to treat the infection after removing the infected prosthesis and, on the other, to protect the joint space until a new prosthesis is implanted in the surgical site from which the infection has been removed. These functions are performed by the spacer device, which is made of a suitable biocompatible material, such as a bone cement based on an acrylic resin, for example polymethyl methacrylate, for example therefore a polymethyl methacrylate (PMMA) based bone cement, possibly with the addition of at least one medical substance with an antimicrobial effect (for example, at least one antibiotic to treat the infection at the implant site). The most commonly used antibiotics are one of gentamicin, vancomycin, and so forth, or combinations thereof.

The antibiotic or blend of antibiotics is mixed with bone cement by the doctor on the basis of, for example, the indications of the pharmacologist who has evaluated the specific bacterial or pathogenic flora of the patient. The resulting material or mass is used to form the most effective spacer device for eradicating the specific infection in the specific patient.

In the following disclosure, the terms "upper" and "lower", and the like, refer to a specific configuration (e.g. opening or closing) of the mold according to the present invention, and do not necessarily remain such when the mold changes to a configuration other than that for which said terms have been indicated.

Figures 30A, 30B, 30C:
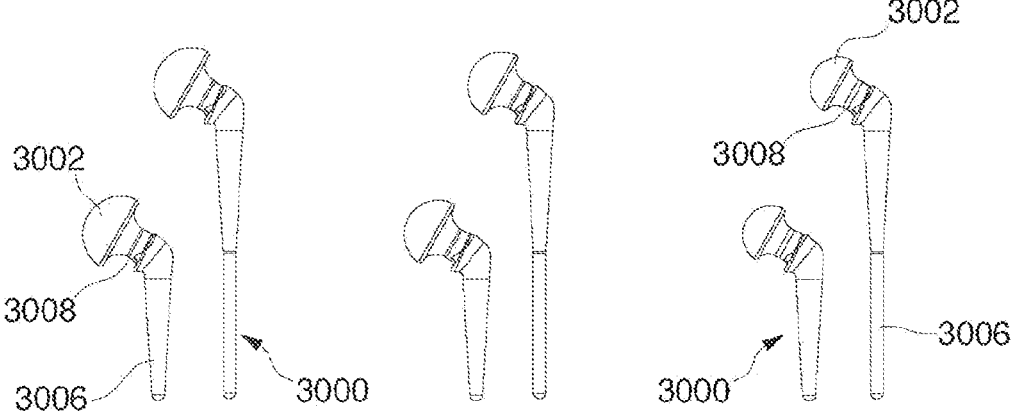
FIGS. 30A, 30B and 30C illustrate side views each of two examples of hip spacer devices (one with a long stem and one with a short stem) obtainable with the mold of the previous figures from 25 to 29, in which the devices of FIG. 30A have a small size (S), the devices of FIG. 30B have a medium size (M) while the devices of FIG. 30C have a large size (L)

FIGS. 1 to 12 show a mold 100 for forming a tibial knee spacer device (the latter shown in FIGS. 13A and 13B), adapted for implantation in use at the tibial bone of the knee joint; FIGS. 14 to 23 show a mold 200 for forming the femoral knee spacer device (the latter shown in FIGS. 24A and 24B), adapted to be implanted in use at the femoral bone of the knee joint; FIGS. 43A to 51B show another version of the mold 200 for forming the femoral knee spacer device (the latter shown in FIGS. 24A and 24B), FIGS. 25 to 29 show a mold 300 for forming a hip spacer device (the latter shown in FIGS. 30A and 30B), adapted for implantation in use at the femoral bone of the hip joint; and FIGS. 31 to 35 show a mold 400 for forming a shoulder spacer device (the latter shown in FIGS. 36A and 36B), adapted in use for implantation at the shoulder joint.

In any way, and as already mentioned, the present invention generally refers to a mold for forming a spacer device and, therefore, unless otherwise explicitly stated, what is disclosed for one version of the invention can also be applied to another version of the invention.

In general, the mold according to the present invention has a shell structure composed of at least two half-shells, which is a rigid structure, i.e. it does not deform when subjected to a force, for example a manual one, and/or to possible reaction forces developed during the forming of the spacer device in question.

In at least one version of the invention, the material that constitutes the mold, although rigid, is free of additives that could be extracted and/or absorbed by the material or by the bone cement that will constitute the spacer device during the forming. The extraction and/or absorption of the additives present in the material of which the mold is made, is a very serious problem that is present, for example, in molds made of elastomers, such as silicone, and so forth. As is evident, if the material of the molded spacer device has in its mass any additives extracted and/or absorbed by the material constituting the mold, this undermines the safety of the spacers molded through such molds from a toxicological point of view. Since 2018, many molds of this type have been withdrawn from the global market.

In one version of the invention, the mold is made of polypropylene.

As will be apparent from the following disclosure, in at least one version of the invention the two half-shells differ from one another in at least one feature. Hence, unless otherwise explicitly stated, the first half-shell and the second half-shell do not mirror each other.

Regarding the forming step, the first half-shell is also called lower body while the second half-shell is also called upper body, one with respect to the other, and considering the support plane on which the mold can rest in the closed configuration during the forming step of the respective spacer device. The second half-shell can therefore act as a cover for the first half-shell.

During the forming step, the mold is in fact in a closed operating configuration, in which the first half-shell is placed on top of second half-shell.

During the loading step of the material the spacer device is made of, however, the mold is in an open operating configuration, e.g. a book-like open configuration. In this case, the first and the second half-shells can both rest on a support plane and/or be placed side by side. In such a way, their forming surfaces, which will be better defined forward, are placed towards the top and are directly accessible by the surgeon or by the operator which has to form the spacer device.

With respect to the first version of the present invention, the mold 100 comprises a first half-shell or lower body 2 and a second half-shell or upper body 4.

The first half-shell 2 and the second half-shell 4 are adapted to be coupled in use so as to define therebetween—thanks to a first and a second forming surface enclosed between them—a cavity 6 corresponding to the external configuration of the spacer device that they are designed to form (specifically a tibial spacer device 1000 for the knee joint and/or a tibial plate 1001).

According to at least one version of the present invention, therefore, the cavity 6 corresponds to the external configuration of the whole spacer device that is designed to form.

The first half-shell 2 and/or the second half-shell 4 have a substantially box-like conformation, and/or a substantially polyhedral and/or parallelepipedal conformation, possibly rectangular or cylindrical. The first half-shell 2 and/or the second half-shell 4 may have a casing and/or block configuration, open from at least one side, or closed and/or may be full or internally hollow.

The faces of the polyhedron and/or the parallelepiped can, for example, be substantially triangular, square or rectangular, possibly with bevelled edges, and so forth. According to an embodiment, two faces are of larger size and lie on two planes parallel to each other and parallel to the support plane on which the mold 100 is adapted to be placed, while the other at least three faces, four in the attached Figures, constitute a side wall which develops along the perimeter of at least one of the faces of larger size, in a substantially perpendicular manner to the latter.

The side wall therefore consists of smaller dimensions faces.

In the case of a cylindrical conformation, on the other hand, there are two substantially larger, circular or oval faces and a side wall, possibly tubular, extending along the perimeter or circumference of at least one of the larger faces.

Thus, the first half-shell 2 comprises at least one upper face 2a and a side wall 2b. There may also be a lower face 2c; alternatively, the first half-shell 2 may be open at the bottom. The upper face 2a and, possibly, the lower face 2c constitute the larger faces of the first half-shell 2.

The mold 100, therefore, has at least one interchangeable insert 15 or a series of interchangeable inserts 15 (for example shown in FIG. 9) comprising more than one or more than two of such interchangeable inserts 15.

The at least one interchangeable insert 15 is removable; it has a given size, in the sense that it is suitable for forming at least a part of the spacer device having a given size.

The at least one interchangeable insert 15 is part of a series of inserts 15 and has a specific size and/or shape, in which this specific size and/or shape is different from the size and/or shape of a second insert belonging to the series of inserts. More in detail, the first and/or second forming surface 8, 10 carried by the at least one insert has a specific size and/or shape, in which this given size and/or shape is different from the size and/or shape of a first and/or second forming surface 8, 10 carried by a second insert belonging to the series of inserts.

Figures 9, 10, 11, 12:
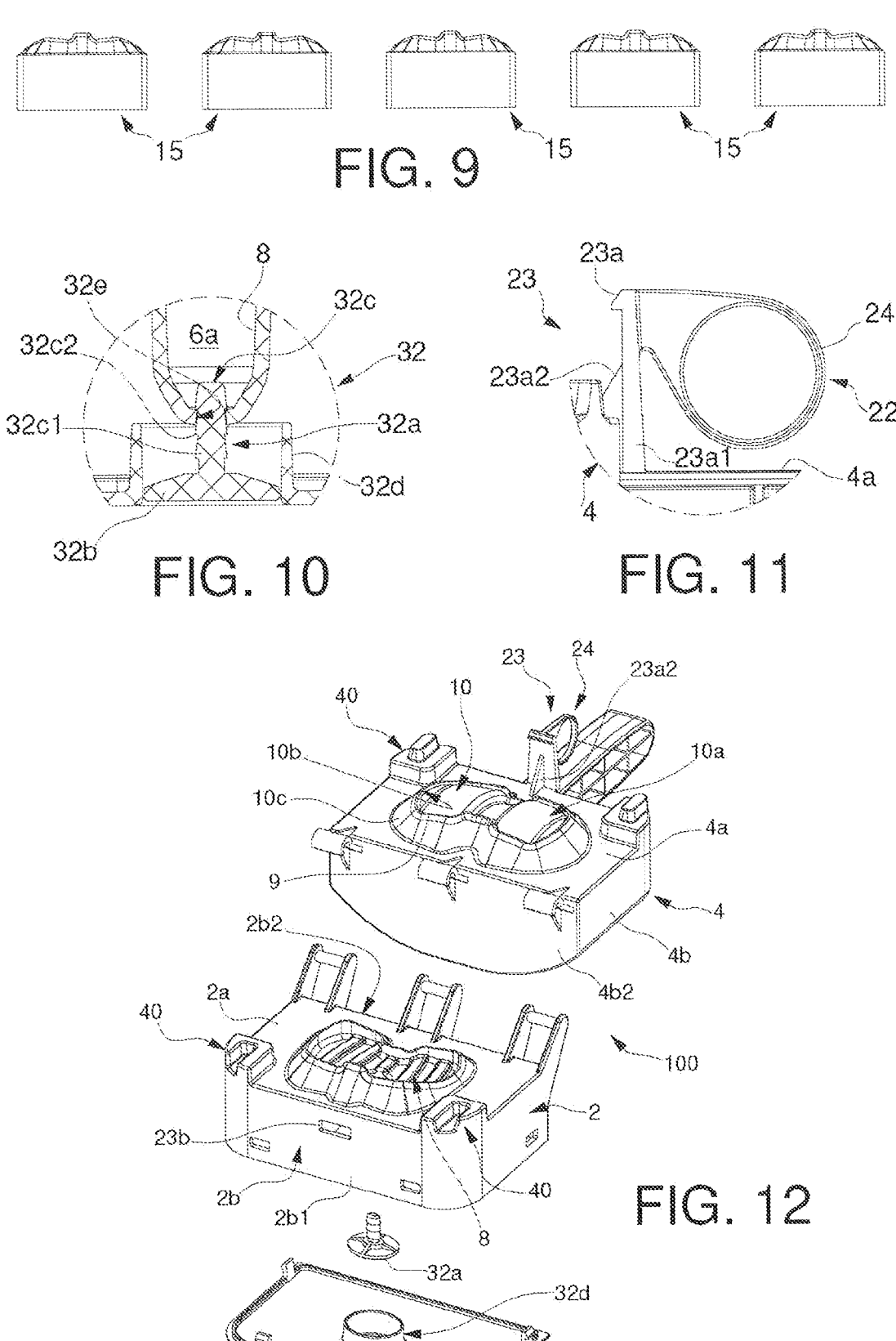
FIG. 9 shows a series of possible inserts of FIG. 6, having, from left to right, respectively a very small (XS), small (S), medium (M), large (L) and very large (XL) size.
FIG. 10 shows an enlarged detail of an element of the mold of FIG. 1.
FIG. 11 shows an enlarged detail of another element of the mold of FIG. 1.
FIG. 12 shows an exploded view of the mold of FIG. 1.
Figure 14:
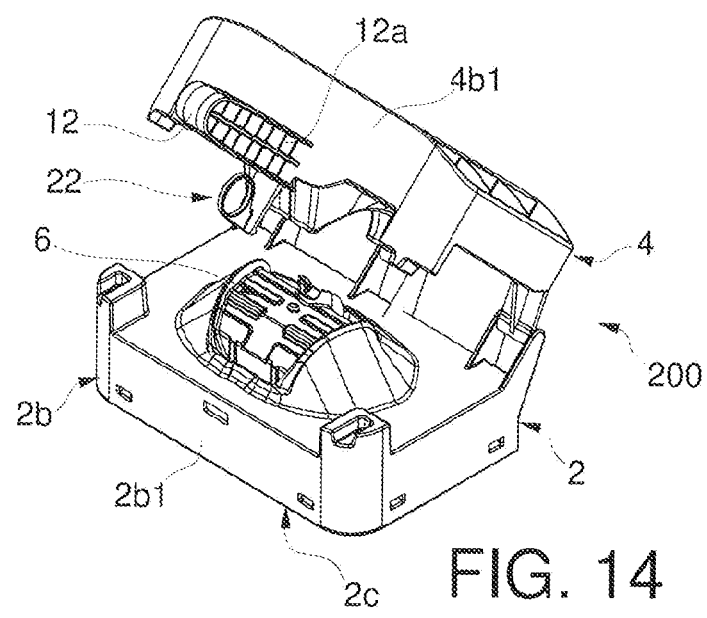
FIG. 14 illustrates a perspective view of a mold for forming a femoral knee spacer device, in a partially open configuration.
Figure 15:
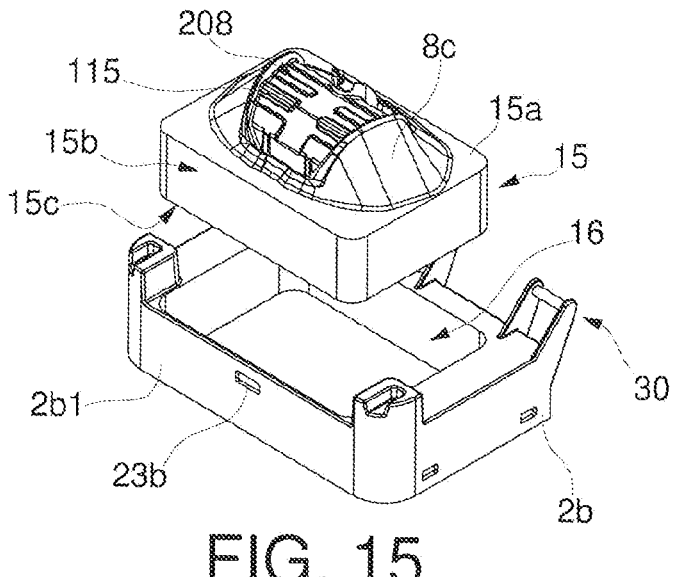
FIG. 15 illustrates a perspective view of a component and an insert of the mold of FIG. 14, in a disassembled configuration.
Figure 16:
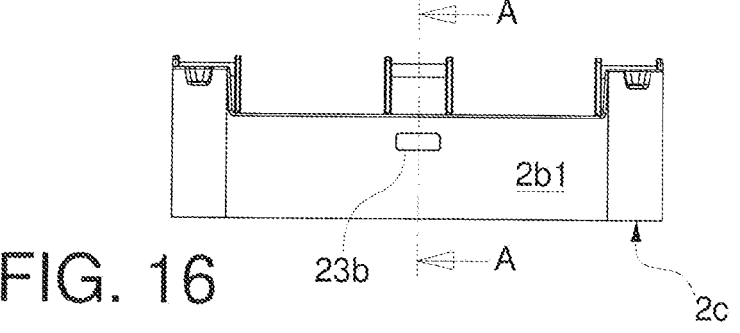
FIG. 16 illustrates a front side view of the component of FIG. 15.

These interchangeable inserts 15, in fact, serve to be able to form, in a single mold, spacer devices of different sizes. For example, FIG. 9 shows, by way of example, from left to right, respectively, inserts relating to a very small (XS), small (S), medium (M), large (L), very large (XL) size, of the respective spacer device that they are capable of forming. Consequently, the first and/or second forming surface has a chosen size, for example, from very small (XS), small (S), medium (M), large (L), very large (XL), or just some of the same.

In fact, it is very important that the spacer device adapts to the real dimensional and anatomical needs of the patient in which it is to be implanted. Thanks to at least one insert 15, the surgeon or the operator responsible for shaping the spacer device can select the insert 15 of the size that best meets the needs of the implantation site.

The insert 15 also has a substantially box-like conformation, and/or a substantially polyhedron and/or parallelepiped, possibly rectangle, or cylinder conformation.

The at least one insert 15 can be solid or internally hollow, furthermore, it can have an enclosure and/or block configuration, open on at least one side or closed.

The faces of the parallelepiped can be, for example, substantially triangular, square or rectangular, possibly with rounded edges, etc. According to an embodiment, two faces are larger in size (for example a first face 15a, in upper use, and a second face 15c, in lower use in the case of the at least one insert of the first half-shell 2) and lie on two parallel planes to each other and parallel to the support surface on which the mold 100 is adapted to be placed, the other at least three faces, four in the attached figures, constitute a perimeter wall 15b, in lateral use, which extends along the perimeter of at least one of the faces of larger dimensions, substantially perpendicular to the latter.

The perimeter wall 15b, therefore, is formed by faces of smaller dimensions.

Also in this case, according to an embodiment example, the second face 15c can comprise an opening, so that the insert 15 is open at the bottom.

In the case of any at least one insert 15 present in the second half-shell 4, the first face 15a, designed to abut with the first face 15a of the at least one insert of the first half-shell 2, is the one in use below. The same applies to the second face 15c, which is in higher use, considering the mold 100 when it is presented in its closed configuration.

The overall and/or bulk dimensions of the at least one insert 15 are smaller than the overall and/or bulk dimensions of the first half-shell 2 (or of the second half-shell 4), since the insert 15 is adapted in use to be housed inside the first half-shell 2 (or the second half-shell 4).

Specifically, the first half-shell 2 and/or the second half-shell 4 comprises at least one seat 16 for housing the at least one insert 15.

The at least one seat 16, therefore, is a recess seat inside the first half-shell 2 and/or the second half-shell 4, with a complementary conformation and corresponding to that of at least one insert 15.

The insert 15 is housed to size inside the seat 16.

In this way, the first half-shell 2 and/or the second half-shell 4 acts as an insert holder, equipped with the seat 16 suitable for housing the insert 15.

Each insert 15 has a forming surface for a respective part of the spacer device to be formed.

In the example shown in the figures, the at least one insert 15 of the first half-shell 2 comprises a first forming surface 8.

The same argument can be made for the eventual (further) at least one insert 15 which can be housed in the second half-shell 4 and for the second forming surface 10 carried by the eventual (further) at least one insert 15. However, this version is not shown in the figures and will be described in detail only for the first half-shell 2, although it is considered applicable, with the variants of the case, also to the second half-shell 4.

According to a version of the invention, therefore, the first half-shell 2 comprises at least one (first) insert 15 housed/ which can be housed in at least one (first) seat 16 made in the first half-shell 2, in which the at least one (first) insert 15 comprises the first forming surface 8, and the second half-shell 4 comprises at least one (further) insert 15 housed/ which can be housed in at least one (second) seat 16 made in the second half-shell 4, in which the at least one (further) insert 15 comprises the second forming surface 10.

In an alternative version, the first half-shell 2 comprises at least one insert 15 equipped with the first forming surface 8 while the second forming surface 10 is present directly in the second half-shell 4 (in the latter case, therefore, the second half-shell 4 does not have at least one insert nor a seat for its housing), or vice versa.

In at least one version of the invention, the first and second forming surfaces 8, 10 are adapted in use to form two transverse portions (i.e. substantially parallel to a transverse plane of the human body) or two longitudinal portions (i.e. substantially parallel to the longitudinal axis) of the resulting spacer device.

The seat 16 and the overall structure of the insert 15 always have the same dimensions, so that each insert 15 can be housed in the corresponding seat 16. What varies is the size of the forming surface carried by these inserts 15.

The first half-shell 2 and/or the second half-shell 4 is therefore "universal" in the sense that it has a seat 16 compatible with all the interchangeable inserts 15. Furthermore, the elements comprised by the mold, which are all provided on the first and/or on the second half-shell, namely—as will be described in more detail below—the handle, the removable restraint structure, the hinge means and the extraction means (when all these elements are present or only some of them), as well as any centerings and other mechanisms, are supplied only once on the first half-shell and/or the second half-shell, but they can be exploited by all the interchangeable inserts and therefore to form spacer devices of all the sizes and conformations needed or wanted.

For the correct functioning of the mold, once the desired size for the spacer device has been selected, the corresponding interchangeable insert 15 is selected, which is positioned on the seat 16 suitable for its housing. In detail, the interchangeable insert can be permanently fixed to the first half-shell 2 and/or to the second half-shell 4 or it can be fixed in a removable way.

In relation to this second option, in at least one version of the invention, the inserts do not have snap-type systems for locking in the right position in the respective housing seat. Indeed, the at least one insert, once positioned, is removable but maintains the right position in the housing seat thanks to a friction fixing created by matching the perimeter surfaces respectively of the at least one insert 15 in the seat 16 with light rubbing.

Once the material that constitutes the spacer device has solidified, it does not detach so easily from rigid surfaces. However, thanks to the fact that the at least one insert is removable, and therefore movable, it can be extracted from the housing seat after forming the space device and, in one at least version of the invention, it is possible to release the spacer device (obtaining an easy detachment) by pushing and/or manually pressing on it and/or on its perimeter side in use wall.

In a further version, in the case of removable inserts, after having formed a spacer device of a certain size by means of an interchangeable insert 15, it is possible to eliminate the insert already used but reuse the first half-shell 2 and/or the second half-shell 4 with at least a different insert, for forming a subsequent spacer device, without losing the characteristics of perfect shape and perfect stability that guarantees a completely disposable mold. In this case, only the inserts 15 are disposable.

The upper face 2a of the first half-shell 2 has the housing seat 16 in a substantially central position. In turn, the first face 15a, upper in use, of the insert 15 has the forming surface 8 in a substantially central position.

In use, i.e. when the insert 15 is housed in its seat 16, the first face 15a of the insert 15 is flush with the upper face 2a of the first half-shell 2.

In a version of the invention, illustrated for example in the figures, in fact, the upper face 2a of the first half-shell consists of an annular surface which extends around the recessed seat 16. When the mold is closed, the first forming surface 8 is superimposed on the second forming surface 10, so as to form the at least one cavity 6.

The first forming surface 8 is delimited by a perimeter edge 7 while the second forming surface 10 is delimited by a perimeter edge 9.

The cavity 6 and/or the first forming 8 and/or the second forming surface 10 has a substantially C-shaped plan conformation, corresponding to that which the resulting tibial spacer device will have.

In particular, the free sections of C are found, as regards the first half-shell 2, at a rear area thereof. However, a different position is possible, without departing from the protection scope of the present invention.

The first forming surface 8 and/or the second forming surface 10 make up the area of application of the material that will constitute the spacer device to be formed with the mold according to the present invention; such forming surfaces are respectively intended to shape at least a first portion and at least a second portion of the spacer device.

In at least one version of the present invention, the first forming surface 8 determines the forming of (and/or is adapted to form in use) a first in use lower portion of the resulting spacer device (in the sense that, at the time of implantation, it will be positioned lower than the human body considered in an upright position).

Similarly, the second forming surface 10 determines the formation of (and/or is adapted to form in use) a second upper in use portion of the resulting spacer device (in the sense that, at the time of implantation, it will be positioned higher than the human body considered in an upright position).

Additionally or alternatively, the first portion can comprise surfaces of the spacer device adapted to come into contact with the patient's bone when implanted, while the second portion can comprise articulating surfaces (for a further spacer component or for a patient's bone) of the resulting spacer device.

Accordingly, the first forming surface 8 is adapted in use to form substantially only patient bone contact surfaces in use of the resulting spacer device while the second forming surface 10 is adapted in use to form substantially only articulating surfaces in use of the resulting spacer device (or vice-versa).

It follows that, in the closed operating step of the mold, considering the spacer device to be formed, the first portion and the second portion are joined together on a plane parallel to a transverse plane of the human body.

Therefore, generally speaking, the first perimeter edge 7 and the second perimeter edge 9 lie—in the closing position of the mold and/or when they are in contact with each other—on a plane parallel to a transverse plane of the human body or on a plane parallel to a transverse plane of the spacer device to be formed.

The first perimeter edge 7 and the second perimeter edge 9 are adapted in use to determine a transverse peripheral profile of the resulting spacer device.

In use, the first perimeter edge 7 is adapted to be brought into abutment against the second perimeter edge 9. During the forming step, therefore, the first perimeter edge 7 is adapted to come into contact with the second perimeter edge 9.

The first forming surface 8 and the second forming surface 10 determine the cavity 6 for forming of the spacer device. Indeed, the first half-shell 2 and the second half-shell 4 engage in a removable way with each other at the respective first perimeter edge 7 and second perimeter edge 9, thereby delimiting the cavity 6 between them.

In at least one version of the invention, the first perimeter edge 7 and/or the second perimeter edge 9 extend along the entire perimeter of the first forming surface 8 and/or the second forming surface 10 respectively (and thus along the entire transverse profile, for example, of the resulting spacer device). In this way, when the first perimeter edge 7 and the second perimeter edge 9 are in contact with each other because the mold 100 is closed, they leave no contact-free zone between them from which material for forming the spacer device could possibly escape, for example by forming machining burrs, without at least one of the first perimeter edge 7 and the second perimeter edge 9 being able to act on said material, for example by cutting it.

Thus, in at least one version of the mold 100, the first perimeter edge 7 is continuous and unique for the entire first forming surface 8 as well as the second perimeter edge 9 is continuous and unique for the second forming surface 10.

In addition, with the exception of the depth gauges 40, which will be discussed below, the first half-shell 2 and the second half-shell 4, in at least one embodiment, come into contact with each other only at the first perimeter edge 7 and the second perimeter edge 9. The latter, therefore, constitute the maximum contact zone between the first half-shell 2 and the second half-shell 4, when the mold 100 is closed. They also constitute the minimum necessary surface of abutment for the correct forming of the spacer device which has to be molded.

At least according one version of the invention, indeed, the first perimeter edge 7 has a minimum contact surface with the second perimeter edge 9, so as to form with the latter a sort of "blade" capable of cutting the forming burrs during the molding and/or forming step.

The first forming surface 8 is made by a (first) base 8a, in recess with respect to the first face 15a of the insert 15 and/or the upper face 2a of the first half-shell 2 and/or the first perimeter edge 7, and a (first) side surface 8b. The side surface 8b develops along the perimeter of the base 8a, from the latter to the first perimeter edge 7. The side surface 8b is perpendicular or inclined towards the outside with respect to the base 8a.

The base 8a and the side surface 8b are internal with respect to the first perimeter edge 7.

The first perimeter edge 7, therefore, is raised with respect to the base 8a and/or to the upper face 2a and/or to the first face 15a.

Figures 1, 2, 13A, 13B:
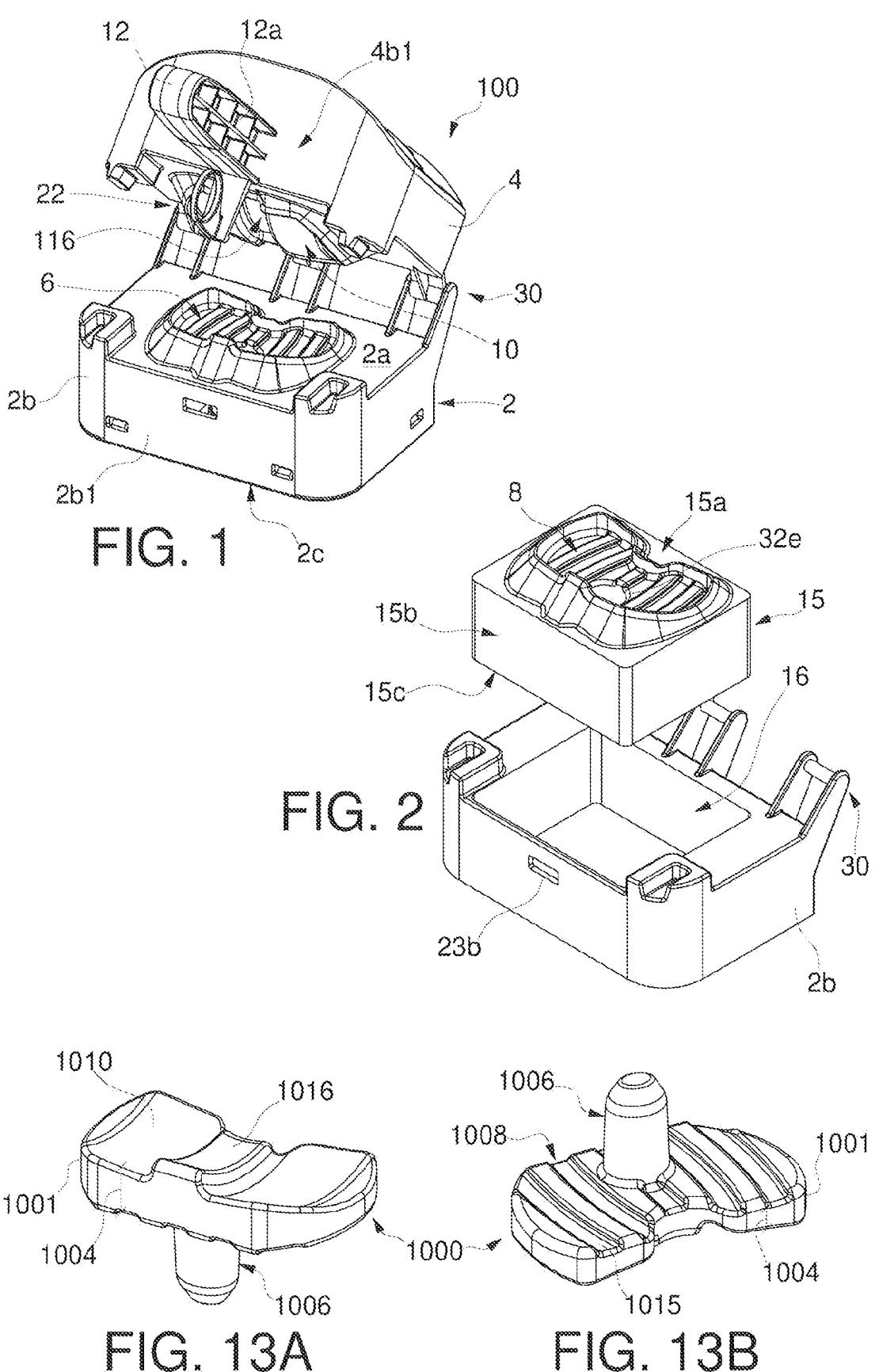
FIG. 1 shows a perspective view of a mold for forming a tibial knee spacer device, in a partially open configuration.
FIG. 2 shows a perspective view of a component and of an insert of the mold of FIG. 1, in a not-assembled configuration.
FIGS. 13A and 13B show perspective views respectively from above and from the bottom of a tibial spacer device obtainable with the mold of previous figures.
Figure 3:
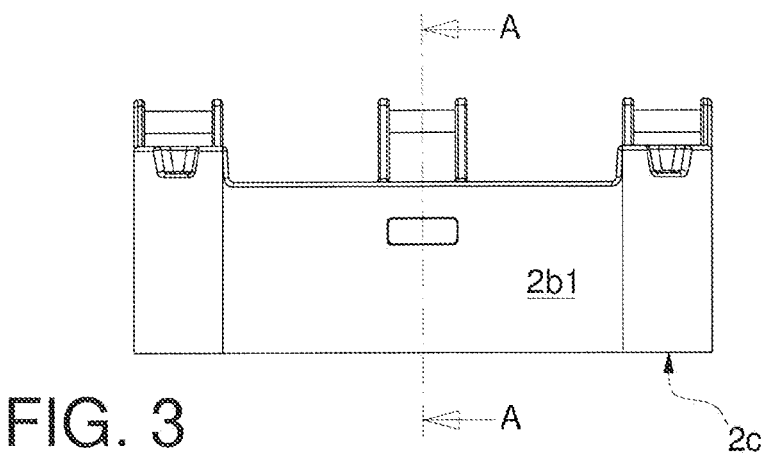
FIG. 3 shows a front side view of the component of FIG. 2.
Figure 4:
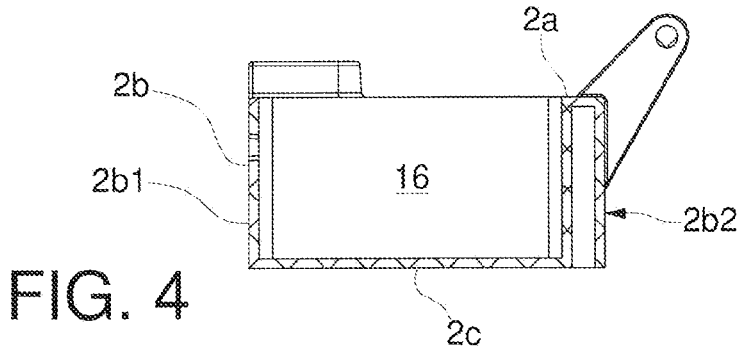
FIG. 4 shows a sectional view taken along the A-A section plane of the component of FIG. 3.
Figure 5:
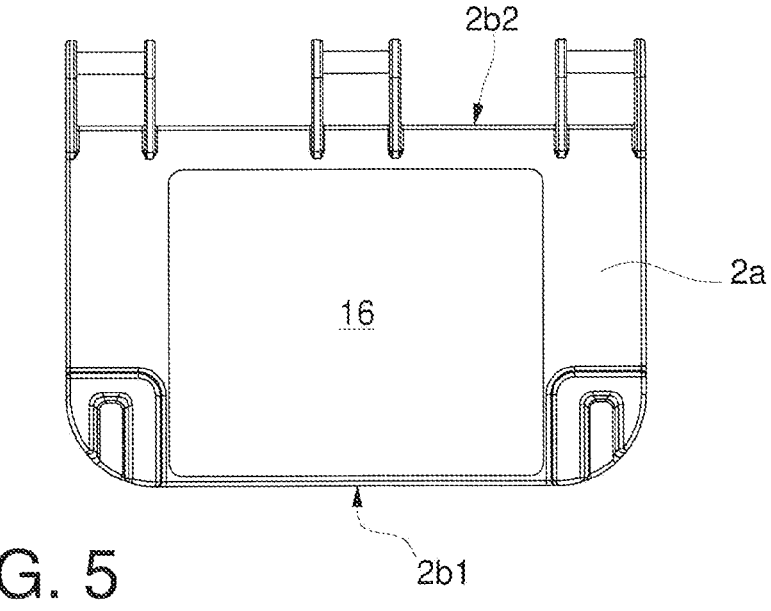
FIG. 5 shows a top view of the component of FIG. 3.
Figure 6:
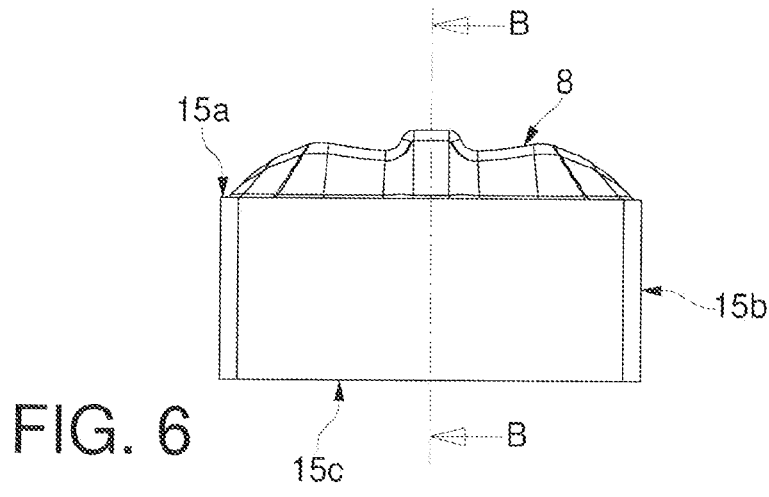
FIG. 6 shows a front lateral view of the insert of FIG. 2.
Figure 7:
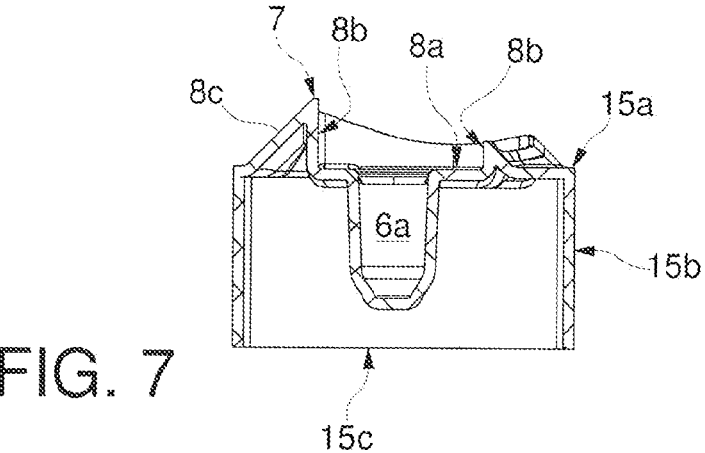
FIG. 7 shows a sectional view taken along the B-B section plane of the insert of FIG. 6.
Figure 8:
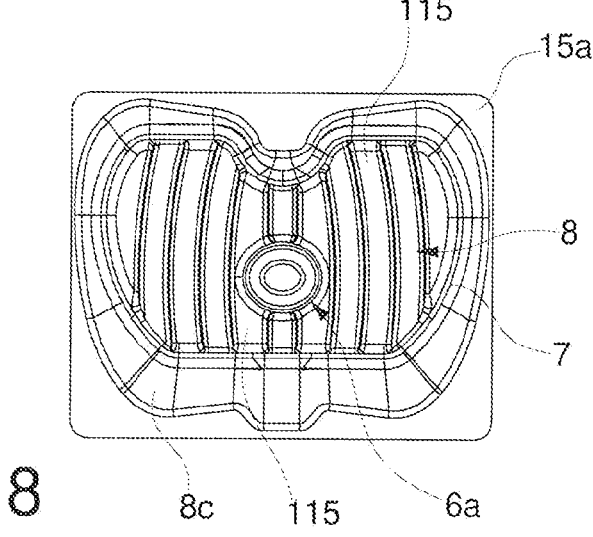
FIG. 8 shows a top view of the insert of FIG. 6.

With particular reference to the Figures indicated, the first forming surface 8 of the mold 100 is adapted to form a portion or lower face 1008 of the tibial knee spacer device 1000, the latter being illustrated in FIGS. 13A and 13B, while the second forming surface 10 is adapted to form a portion or upper face 1010 of the spacer device 1000.

The upper face 1010 is adapted in use to be articulated with a femoral knee spacer device (such as that illustrated in FIGS. 24A and 24B or a generic femoral knee spacer device) or with the femoral end of a knee joint of a patient, while the lower face 1008 is adapted in use to be implanted at the end of the patient's tibial bone at the knee joint.

The spacer device 1000 may also comprise a stem 1006, possibly formed by means of a special additional cavity 6a (visible, for example, in FIG. 7 and partially in FIG. 10) placed at the first forming surface 8.

The cavity 6 therefore substantially determines the formation of the tibial plate 1001 that has a substantially rectangular or oval or C-shaped conformation in the plan view and a thickness 1004 given by the distance between the lower face 1008 and the upper face 1010 of the spacer device 1000. The cavity 6a substantially determines the shaping of the stem 1006. However, the cavity 6 and the additional cavity 6a are contiguous to each other and/or in fluid connection, so that the material that will form the spacer device 1000 can be inserted and/or flow (during the forming step) into both said cavities 6, 6a and, in one step, form both the tibial plate 1001 and the stem 1006 of the spacer device 1000.

In an alternative version of the invention, the first half-shell 2 and the second half-shell 4 are substantially the same and mirror each other. It follows that the first forming surface 8 and the second forming surface 10 are substantially the same and mirror each other.

In this case, the first molded portion and the second molded portion of the resulting spacer device are identical and mirror each other, joined at a median plane of symmetry (for example parallel to a sagittal plane of the human body). In use, the first perimeter edge 7 and the second perimeter edge 9 of the mold 100 lie along the median plane of symmetry of the resulting spacer device.

In this version, in the resulting spacer device both the first and the second forming surfaces are each adapted to form contact surfaces with the patient's bone and joint surfaces.

A handle 12, possibly removable, is located at the second half-shell 4 of the mold 100.

The surgeon or the personnel in charge of forming the spacer device 1000 by means of the mold 100 will in fact use this handle 12 to bring the first half-shell 2 into abutment against the second half-shell 4 (or vice-versa) and to apply adequate force to compress the material that will constitute the spacer device itself. Indeed, the mold 100 is not an injection mold and the loading of the material to be molded into the mold 100 will be illustrated in greater detail in the continuation of the present disclosure.

For this purpose, the step of filling the mold with the material that will constitute the spacer device, or with the bone cement, does not require auxiliary accessories such as injection or pressurisation systems (specific syringes).

On the other hand, these accessories are necessary for the molds currently available on the market and often involve an additional cost and a definite complication in use, and increase the defectiveness of the molded device due to the presence of bubbles always associated with the use of syringes. Therefore, filling these injection molds necessarily requires a very fluid cement that is injected, flows smoothly but, while filling the mold, encapsulates air that creates bubbles of various sizes. Following hardening of the cement, these bubbles leave many cavities, hence negative defects, on the surface of the molded device, making its shape incomplete.

In contrast, with the mold of the present invention, filling is done manually, using, for example, a cement which has reached a high ideal viscosity established by a standard test called "doughing time". Doughing time establishes the right viscosity so that the surgeon can take the cement from the mixing vessel and manipulate it for application without damaging it (the test is defined by ISO 5833/1 Second edition 2002-05-01 Implants for surgery—Acrylic resin cements—Implant chirurgicaux—Ciment á base de résine acrylique, page 7). This condition, easily repeatable in all operating theatres in which the bone cement and/or the mold according to the present invention is used, makes possible the safe use of the cement while obtaining a resulting defect-free molded device.

This is an important simplification of use because it takes advantage of traditional bone cement preparation while achieving the desired results.

The handle 12 has a substantially elongated and possibly ergonomic conformation, so as to be easily gripped by an operator's hand. The shape of said handle 12, therefore, has a substantially rectangular longitudinal section, with bevelled edges (as seen, for example, in FIG. 1), while the cross section thereof can be substantially rectangular, square, circular, triangular, and so forth.

By "longitudinal section" is meant that section taken along a plane that is perpendicular to the mold along the longest dimension of the handle, while by "cross section" is meant that section taken along a plane that is perpendicular to the mold along the shortest dimension of the handle.

The handle 12 may internally comprise reinforcing elements 12a, for example ribs (as shown in FIG. 1), in order to ensure better resistance to the forces applied to close the two half-shells 2, 4 of the mold 100 and the consequent forming of the spacer device 1000.

In general, at least one of (or both) the first perimeter edge 7 and the second perimeter edge 9 is raised with respect to the first half-shell or lower body 2 and the second half-shell or upper body 4, respectively.

The first face 15a of the at least one insert, therefore, is connected to the first peripheral edge 7 by means of a (first) raised wall 8c. The raised wall 8c is substantially inclined or perpendicular to the first face 15a and/or to the upper face 2a of the first half-shell 2 and, in at least one version of the invention, extends away from the first peripheral edge 7 and/or from the base 8a and/or from the first forming surface 8. The raised wall 8c is positioned externally to the peripheral edge 7 with respect to the forming surface enclosed by it.

The remaining part of the upper face 2a and/or of the first face 15a, in at least one version of the invention, is flat and substantially coplanar.

Naturally, together with the base 8a, the side surface 8b also contributes to the shape of the tibial spacer device resulting from forming in said mold 100. Thus, the base 8a and the side surface 8b will be conformed correspondingly, albeit negatively, to at least the lower face 1008 and to at least part of the thickness 1004 of the tibial plate 1001.

Furthermore, at the substantially centrally positioned base 8a, there is an opening to the additional cavity 6a for the stem 1006 of the spacer device in question.

In particular, the base 8a may have a series of first ribs 115 adapted to determine the formation of respective first longitudinal grooves 1015 of the lower face 1008 of the tibial plate 1001.

In a substantially similar way, the second half-shell or upper body 4 comprises at least one lower face 4*a*, adapted to house in a substantially central position the second forming surface 10 and/or at least one insert 15, and a side wall 4*b*. An upper face 4*c* may also be present; alternatively, the second half-shell 4 may be open at the top (considering the closed conformation of the mold).

The second forming surface 10 is made by a (second) base 10*a*, which at least partially rises with respect to the lower face 4*a* and/or to the first face 15*a* of the respective insert 15. In one version of the invention and/or in at least some areas thereof, the base 10*a* rises from the lower face 4*a* and/or to the first face 15*a* to a greater extent than the second perimeter edge 9. The latter can therefore be positioned—as far as the height is concerned—between the most protruding point of the base 10*a* and the lower face 4*a* and/or the first face 15*a*.

The second forming surface 10 further comprises a (second) side surface 10*b*. The side surface 10*b* extends along the perimeter of the base 10*a*, from the latter to the second perimeter edge 9. The lateral surface 10*b* is perpendicular to or inclined towards the outside with respect to the base 10*a*. The second perimeter edge 9 is thus raised with respect to the lower face 4*a* and/or in general with respect to the second half-shell 4 and/or with respect to the first face 15*a* of the at least one insert 15.

Naturally, together with the base 10*a*, the side surface 10*b* also contributes to the shape of the tibial spacer device resulting from forming in said mold 100. Thus, the base 10*a* and the side surface 10*b* will be shaped in a manner corresponding, albeit negatively, to at least the upper face 1010 and to at least part of the thickness 1004 of the tibial plate 1001.

In particular, the base 10*a* can have a substantially smooth surface, although, in at least one version of the invention, comprising a longitudinal central recess 116 corresponding to a substantially rectangular base protrusion 1016 present at the upper face 1010 of the tibial plate 1001.

The lower face 4*a* of the second half-shell 4 and/or the first face 15*a* of the at least one insert 15 is thus connected to the second perimeter edge 9 by a (second) raised wall 10*c*.

The raised wall 10*c* is substantially inclined or perpendicular to the lower face 4*a* and/or the first face 15*a* and, in at least one version of the invention, moves away from the second perimeter edge 9 or the second forming surface 10.

In at least one version of the invention, the remaining part of the lower face 4*a* and/or of the first face 15*a* is flat and substantially coplanar.

At the side wall 2*b* of the first half-shell 2 and the side wall 4*b* of the second half-shell 4, it is possible to identify a (first) front in use area 2*b*1 and a (second) front in use area 4*b*1 and a (first) rear in use area 2*b*2 and a (second) rear in use area 4*b*2.

In a version of the invention, the rear in use area 2*b*2 and 4*b*2 is opposite the front in use area 2*b*1 and 4*b*1.

The handle 12 can be positioned at the front in use area 4*b*1 of the second half-shell 4.

In addition, a removable constraining structure 22 can be positioned at this area, adapted to be constrained in a removable way to the first half-shell 2.

In particular, as illustrated for example in the enlarged detail of FIG. 11 (taken from FIG. 12), the removable constraining structure 22 comprises coupling means 23, for example snap-on, and possibly a trigger element 24.

In at least one version of the invention, the removable constraining structure 22 also comprises the handle 12.

The removable coupling means 23 include, for example, a tooth or protrusion element 23*a*, adapted to engage in a removable way in a suitable engagement seat 23*b*. The engagement seat 23*b* is placed, for example, at the front in use area 2*b*1 of the side wall 2*b* of the first half-shell 2.

Naturally, it is also possible for the coupling means 23 to be placed in a different position than that indicated above. For example, the tooth or protrusion element 23*a* could be positioned at the first half-shell 2 and the engagement seat 23*b* could be positioned at the second half-shell 4.

The coupling means 23 may comprise a special bracket 23*a*1 adapted to carry the tooth or protrusion element 23*a*. Said bracket 23*a*1 has an elongated conformation that departs from the second half-shell 4 for a length such as to be able to bring the tooth or protrusion element 23*a* to the engagement seat 23*b*, when the second half-shell 4 is placed on top of the first half-shell 2 to close the mold 100 and then start the forming step of the spacer device 1000.

This bracket 23*a*1 has, for example, a substantially rectangular shape in the plan view, and a length greater than its width, in turn greater than its thickness. Thus, the bracket 23*a*1 may be long and thin.

As previously mentioned, a first end or zone of the bracket 23*a*1 is stably constrained to the second half-shell 4 and/or the handle 12, while a second end or zone thereof, opposite the first end or zone, for example further away than the second half-shell 4, carries the tooth or protrusion element 23*a*.

The tooth or protrusion element 23*a* is present in the first face of the bracket 23*a*1 which, when the mold 100 is closed, faces in use the first half-shell 2.

In a position opposite to the tooth or protrusion element 23*a*, and therefore for example on the second face of the bracket 23*a*1, opposite the first face, second face which, in use, when the mold is closed, is facing away from the first half-shell 2, the trigger element 24 may be positioned. Otherwise, the trigger element 24 may be carried directly by the handle 12 or other suitable structure.

When the operator in charge of forming the spacer element closes the mold, bringing the first half-shell 2 and the second half-shell 4 into abutment against each other so as to form the cavity 6 between the first forming surface 8 and the first perimeter edge 7 and the second forming surface 10 and the second perimeter edge 9, he/she does so using the handle 12. By applying a for example manual force on the handle 12, he/she can hook on the tooth or protrusion element 23*a*, for example inside the engagement seat 23*b*, due in part to the bracket 23*a*1.

Once the forming step has been completed, and therefore after having waited a predetermined time for the hardening of the material that constitutes the spacer device, the operator acts on the trigger element 24 to determine the release and/or uncoupling of the tooth or protrusion element 23*a* from the engagement seat 23*b*. Since the trigger element 24 is in the vicinity of the handle 12, the operator can, in substantially one-step, grip the handle 12, release the coupling means 23 using the trigger 24, move the second half-shell 4 away from the first half-shell 2 and, by rotating with these two with respect to each other, again using the handle 12, cause the mold 100 to open.

The bracket 23*a*1 may further comprise a stiffening rib 23*a*2, for example sail-shaped or triangular, located at the first face of the bracket 23*a*1. This stiffening rib 23*a*2 helps to support the force applied by the operator to close the mold 100, as well as the force needed during the forming step to keep the mold closed.

The engagement seat 23*b*, for example having a rectangular or circular opening placed at the wall of the half-shell in question, is shaped in a substantially corresponding and/or complementary manner to the tooth or protrusion element 23*a*, so that when the mold 100 is closed, the tooth or protrusion element 23*a* is inserted, possibly snapped-on, inside the engagement seat 23*b*.

Connection between the engagement seat 23*b* and the tooth or protrusion element 23*a* is also obtained on account of the deformability of the material that makes possible the movement toward the engagement seat 23*b* of the tooth or protrusion element 23*a* with the insertion and/or coupling and/or snapping of the same into the seat 23*b*.

In this way, a (temporary) constraint is created between the first half-shell 2 and the second half-shell 4 that makes possible a perfect closure of the mold 100, which is also able to resist any forces of forming and/or polymerisation and/or hardening of the material that makes up the spacer device and that is inserted into the mold itself. Once the formation and/or the polymerisation and/or the hardening of the spacer device is completed, the mold 100 can be opened, by moving the first half-shell 2 and the second half-shell 4 reciprocally away from each other, causing, possibly in a manual way, the exit and/or the release of the tooth or protrusion element 23*a* from the engagement seat 23*b*. In one embodiment, the tooth or protrusion element 23*a* acts as a hook to constrain temporarily to each other the two half-shells 2, 4 forming the mold 100.

The trigger element 24 has a substantially circular or semi-circular or ergonomic conformation, adapted for the insertion of at least one finger of the operator in charge of forming the spacer device. In this way, the operator can act manually on the trigger element 24. A force may be applied on the trigger element 24 in particular, e.g. pushing or pulling, which may cause the tooth or protrusion element 23*a* to exit the engagement seat 23*b*.

As can be seen from the Figures, and as indicated, the tooth or protrusion element 23*a* and/or the trigger element 24 rises from the second half-shell 4 by a distance such as to make possible the insertion of the tooth or protrusion element 23*a* into the engagement seat 23*b* once the mold 100 is closed.

Again as can be seen, as a result of this arrangement the mold according to the present invention has no screws for fixing the first half-shell to the second half-shell and does not even require presses to hold the two half-shells together during the molding step of the spacer device. Both the coupling and the joining of the two half-shells are determined by the presence of the removable constraining structure 22 of the present invention.

There are hinge means 30 in at least one version of the invention, for example at the rear in use area 2*b*2 of the first half-shell 2 and/or at the rear in use area 4*b*2 of the second half-shell 4. These hinge means 30 allow reciprocal rotation (on a special fulcrum or centre of rotation) of the second half-shell 4 with respect to the first half-shell 2, bringing them into abutment with each other and thus determining the closure of the mold 100. Conversely, said hinge means 30 also allow the release rotation between said first half-shell 2 and said second half-shell 4, determining the opening of the mold 100.

In this step, the first forming surface 8 and the second forming surface 10 move away from each other while in the mold closing step they approach each other, until the cavity 6 and, possibly, the additional cavity 6*a*, are determined.

Thanks to the presence of the hinge means 30, it is possible to ensure perfect coupling between the first perimeter edge 7 of the first half-shell 2 and the second perimeter edge 9 of the second half-shell 4.

In particular, at least according to one version of the present invention, the mutual approach of the second forming surface 10 to the first forming surface 8 takes place in a substantially parallel manner, at least in the last part of the mold closing step. In this way, there is a perfect superimposition of the second forming surface 10 to the first forming surface 8, and the consequent determination of a cavity 6 of the exact desired dimensions and conformation for the resulting spacer device.

If desired, to allow the closure of the mold 100, the hinge means 30 can be carried by a suitable bracket connected to the first half-shell 2 and/or to the second half-shell 4, so as to allow the correct positioning of the first perimeter edge 7 on the second perimeter edge 9. The special bracket, in fact, takes into account how much the first perimeter edge 7 and/or the second perimeter edge 9 protrude from the first face 15*a* respectively upper and/or lower in use of the at least one interchangeable insert 15 and/or from the lower face 4*a* of the second half-shell and from the upper face 2*a* of the first half-shell 2.

The appropriate bracket exits the first half-shell 2 and/or the second half-shell 4 so that the hinge means 30 are positioned outside the overlapping surfaces of the mold, for example in detail outside the first half-shell 2 at its side wall 2*b* and/or the rear in use area 2*b*2 thereof. Similarly, a second special bracket may be present at the second half-shell 4, wherein said second special bracket is outside the second half-shell 4 at its side surface 4*b*, for example in detail outside its rear in use area 4*b*2.

Obviously, the first and second special brackets are shaped in a corresponding way, so as to allow the correct functioning of the hinge means 30.

Moreover, the fulcrum or axis of rotation of the hinge means 30, also by means of the suitable brackets, is positioned "offset" with respect to the plane joining the first forming surface 8 and the second forming surface 0 and/or the first half-shell 2 and the second half-shell 4. This means that the fulcrum or axis of rotation is located on a different plane with respect to the joining plane. The joining plane and the plane on which the rotation axis lies are separated by a distance corresponding to the length, for example, of the special bracket present in the first half-shell 2.

In this way, in at least one version of the invention, the forces of polymerisation and/or hardening of the material that forms the spacer device, forces possibly also caused by the counter-reaction of the compression pressure occasioned by the closure of the mold and that would tend to open the mold, are at least in part absorbed by the structure of the mold itself and, due to the positioning of the fulcrum or axis of rotation of the hinge means 30, are of a lower intensity than if the hinge means 30 were positioned at the plane joining the first half-shell 2 and the second half-shell 4.

Indeed, as mentioned, the first perimeter edge 7 and the second perimeter edge 9 abut against each other when the mold is closed, guaranteeing a substantially sealed closure and maintaining a complete contact and/or a complete adhesion between each other along their entire extension. Thus, the first perimeter edge 7 is in abutment against and/or is matches and/or corresponds to the second perimeter edge 9. In this way, the spacer device resulting from the forming step does not require further finishing or cutting steps of the molding burr. In fact, the perimeter edges 7 and/or 9 act almost like a device that cuts the molding burr directly during the forming step.

At least one of the first perimeter edge 7 and the second perimeter edge 9, therefore, is an abutting cutting edge.

Furthermore, when in contact, the perimeter edges 7 and 1 make possible a substantial continuity of the first forming surface 8 with the second forming surface 10. This means that no spaces or gaps are created between the first perimeter edge 7 and the second perimeter edge 9, which could, if present, be invaded by the material constituting the spacer device during the forming step thereof, creating molding burrs that would subsequently have to be eliminated. At the same time, the cavity 6 determined by the first and second forming surfaces 8, 10, for example when the first perimeter edge 9 abuts against and/or contacts the second perimeter edge 9, corresponds exactly to the shape of the spacer device to be formed, without edges or irregularities that would then require polishing or surface finishing work on the spacer device itself.

In one version of the invention, the two edges 7, 9 have flat abutment surfaces that come into direct contact with each other. These abutment surfaces may be substantially parallel to the support plane of the mold 100 or both have the same inclination, outward or inward, with respect to the cavity 6.

In an alternative version, the flat abutment surfaces of the first perimeter edge 7 and the second perimeter edge 9 are both inclined, one outward and the other inward, with respect to the cavity 6. In this case, too, they manage to leave no gaps with respect to the cavity 6, thus eliminating the formation of molding burrs or reducing them to a minimum, since they are cut during the molding process.

In an alternative version, the first perimeter edge 7 has an abutment surface, which may be flat, for example, while the second perimeter edge 9 has an abutment seat shaped into an area for receiving and/or housing the first perimeter edge 7 (or vice-versa). The above-mentioned results can also be achieved in this way.

In detail, the contact between the first perimeter edge 7 and the second perimeter edge 9 determines the burr-cutting function of these edges.

The minimum support surface present between the two edges 7, 9 (and consequently between the first half-shell 2 and the second half-shell 4, each possibly equipped with at least one insert 15) ensures that the force applied in closing (possibly by acting on the handle 12 and/or by means of the removable constraining structure 22) is sufficient to cut and/or divide the material necessary for the formation of the spacer device from the surplus material that escapes into the space outside the cavity 6, beyond the edges 7, 9 themselves.

In a version of the invention, the first perimeter edge 7 and the second perimeter edge 9 are unique and continuous, along the entire perimeter respectively of the first and second forming surface 8, 10.

"Minimum contact surface" means the minimum surface necessary to guarantee the stability of the structure and its ability to withstand the forces applied to it, as well as to guarantee the correct closure of the forming cavity and the correct positioning of the first and second forming surfaces in relation to each other.

The first and the second perimeter edges are adapted to constitute, in use, a single and continuous peripheral edge (transverse or longitudinal) of the resulting spacer device.

In an alternative version, there are no hinge means 30 and first half-shell 2 and second half-shell 4 are moved away from and/or brought closer to each other according to other methods known in the field.

In at least one version of the invention, the mold 100 can also comprise extraction means 32.

The extraction means 32 in at least one version of the invention are placed in at least one inert 15 or in each insert 15, when they are in number higher than one. In at least one version, the extraction means 32 are placed in the second half-shell 2 and/or in the at least one insert 15 present in the second half-shell 2.

The extraction means have the function of extracting the spacer device (once it has been formed and once, therefore, the material of which it is composed has hardened). In addition, since they are unidirectional and/or non-return type extraction means, they have a non-return geometry that makes the mold 100 of disposable type and/or the at least one insert 15 of disposable type.

This aspect is very important because, after having formed a spacer device, the mold might undergo changes or alterations caused precisely by the polymerisation and/or hardening reaction of the material that constitutes the device itself and which could compromise its correct functioning. Such a mold should therefore not be re-used more than once. In the event of re-use, the two half-shells and the other components need to be sterilised and the sterilization step too could cause modifications or alterations that could compromise its correct functioning.

Again, only the use of disposable molds guarantees optimal sterilisation thereof.

As can be seen, for example in FIG. 10, which represents an enlarged detail of the mold 100, and in FIG. 12, the extraction means 32 comprise a button element 32a equipped with a pressing body 32c1 comprising a base 32b and a tip or end 32c.

The pressing body 32c1 has a substantially pin or peg conformation which extends from the base 32b and ends with the tip or end 32c. The base 32b is opposite the tip or end 32c.

The base 32b is placed at the lower face 2c of the first half-shell 2, possibly flush with the latter. The tip or end 32b is positioned at the additional cavity 6a, in particular at the most distal region of this additional cavity 6a.

From the version visible in FIG. 10, and which may be absent in other versions, during the forming step the tip or end 32c of the pressing body 32c1 is positioned inside the additional cavity 6a and therefore occupies a small part of the space intended for formation of the stem 1006. Accordingly, at the distal end of the stem 1006 there may be a small cavity, created precisely by such a tip or end 32c.

In a version in which the additional cavity 6a is not present, the tip or end 32b is placed at the cavity 6.

A space 32d is also envisaged at the lower face 2c of the first half-shell 2, for example a box-like or ring (possibly open at least at one more outer side with respect to the first half-shell 2, or in a version open both at the lower face 2c and at one end opposite thereof) space, the cross-section of which corresponds to the cross-section of the (e.g. circular) base 32b and the height of which corresponds to the stroke of the button element 32a.

In use, the operator in charge of the formation of the spacer device, once the latter has been formed, will press, for example manually, on the base 32b of the button element 32a (which in a first configuration is flush with the lower face 2c and is accessible through a special opening located at the space 32d), so that the tip or end 32c presses against the stem 1006 or against the lower face 1008 of the tibial plate 1001 and determines the ejection of the spacer device formed by the mold 100 and/or the cavity 6 of the first half-shell 2.

The height of the space 32d is therefore lower than or equal to the height of the pressing body 32c1 and/or is lower than that of the button element 32a.

As can be seen from the detail of FIG. 10, the pressing body 32c1 may have a series of lateral protrusions 32c2 extending externally from the pressing body 32c1 and shaped, for example, like a dovetail.

The button element 32a and/or the pressing body 32c1 and/or the lateral protrusions 32c2 are made of a deformable material, which allows the passage of the tip or end 32c through a special hole 32e present at the additional cavity 6a or the cavity 6 when the button element 32a is pressed to extract the spacer device, but do not allow it to escape or return to position. In this way, the pressing body 32c1 remains inside the additional cavity 6a or the cavity 6, effectively preventing a second or subsequent use of the mold 100 and/or of the at least one insert 15.

Conversely, with reference to FIGS. 45B, 48 and 50B to 51B, extraction means 232 may be present. They comprise a pressing body 32c1 comprising a base 32b and a tip or end 32c.

The pressing body 32c1 has a substantially pin or peg conformation and a thread adapted to engage, in a unidirectional manner, with a special seat 33 (possibly corresponding to the space 32d) located at the first half-shell 2, substantially in a central position with respect to the first forming surface 208.

The seat 33 has a nut screw (or further threading) corresponding to the threading of the pressing body 32c1.

The extraction means 232 can also comprise a cap or lid 34 that can be housed and/or positioned at the tip 32c.

Such a cap or lid 34 can be housed, for example snapping-on, in a suitable seat or opening 34a located at the first forming surface 208, in communication with the cavity 6 and/or at the seat 33.

The cap or cover 34 engages with a relative seat present at the tip 32c of the pressing body 32c1.

The extraction means 232 further comprise a handle element 35 capable of being grasped by the operator for the purpose of screwing the extraction means into their seat 33.

Overall, the extraction means 232 have a substantially key-shaped conformation.

As can be seen in FIG. 45B, when the extraction means 232 is screwed into the seat 33, it comes into contact with the cap or lid 34. While screwing, the pressing body 32c1 presses against the cap or lid 34; the latter presses against the formed spacer device and causes it to detach from the mold 200 and/or the first half-shell 2.

Between the pressing body 32c1 and the handle 35 there is a discoidal base 36 adapted to comprise at least a pair of teeth 36a made of flexible material. Said teeth 36a are adapted to make it possible to rotate the extraction means 232 but not to allow their unscrewing. In this way, there is additional assurance that the mold is in fact disposable.

The teeth 36a are suitable for engaging, for example in rotational screwing mode and/or during screwing of the pressure body 32c1, with respective couplers 36b, located at the seat 33.

Such couplers 36b are adapted to block the unscrewing of the extraction means 232, as they do not allow the passage of the teeth 36a during unscrewing.

For example, the teeth 36a have a C or L shape, so that they deform and can pass over the couplers 36b when screwing in, but block and prevent passage when unscrewing.

The cap or lid 34 is positioned prior to the positioning of the material that will form the spacer device or bone cement and also serves to make the first forming surface 208 substantially continuous.

These extraction means 232 may also be present in other versions of the mold according to the present invention.

Again, in one version of the invention, the second forming surface 10 of the at least one insert 15 of the second half-shell 4 has no undercuts. Thus, once molded, the spacer device will remain constrained (albeit temporarily) only to the first forming surface 8 of the at least one insert 15 of the first half-shell 2 and to the cavity 6. In this way, it is easier to remove the spacer device formed by the first half shell 2, for example using the extractor means 32.

In a further version, if the second forming surface 10 also has undercuts and/or cavities, suitable extraction means (not illustrated) could also be provided from the second half shell 4 or application of detaching means could be contemplated, at least on the second forming surface 10 (or possibly also on the first forming surface 8), such as to facilitate the detachment of the spacer device after its formation.

As said, depth gauges 40 may be present at the upper face in use 2a and/or the lower face 4a of the first half-shell 2 and the second half-shell 104, respectively, for example at the corners of face 2a and/or face 4a at the front area in use 2b1, 4b1 of the same. In an alternative or additional way, such depth gauges 40 may of the sides of the faces 2a and 4a (considering the sides as the surfaces that extend between the front area in use 2b1, 4b1 and the rear area in use 2b2, 4b2 of the first half-shell 2 and/or the second half-shell 4).

Such blocks 40 may have complementary shapes between depth gauges present at the first half-shell 2 and depth gauges present in the second half-shell 4 or between depth gauges present at the first half-shell 2 or relative seats present at the second half-shell 4 (or vice-versa), so as to facilitate closure of the mold 100 and maintenance of the correct forming space when the second half-shell 4 is closed onto the first half-shell 2.

The depth gauges 40 may protrude respectively from the upper face 2a and/or the lower face 4a or at least some depth gauges 40 may be recessed into the upper face 2a and/or the lower face 4a.

The depth gauges 40 may preferably be even in number, e.g. two or four or more for each half-shell 2, 4.

They can be positioned in a corresponding and reciprocal way in the first half-shell 2 and in the second half-shell 4. For example, there may be two blocks 40 in the upper face 2a at the front area in use 2b1 of the first half-shell 2 and two blocks in the lower face 4a at the front area in use 4b1 of the second half-shell 4.

In at least one version, the depth gauges 40 can determine the realisation, when the mold is closed, of a space between upper face 2a of the first half-shell 2 and upper face 4a of the second half-shell 4 in which the material that will make the spacer device can possibly flow, if present in excess of the amount required for forming the spacer device.

As a result of the presence of the first perimeter edge 7 and the second perimeter edge 9, which according to at least one version are raised respectively with respect to the first half-shell 2 and the second half-shell 4, excess and leaking material will be eliminated (cut) when the same edges are brought into contact with each other and the two half-shells 2, 4 are brought into abutment and tightened together, for example by means of the removable constraining structure 22. The cut and/or excess material can be deposited in the space created by the fact that the first perimeter edge 7 and the second perimeter edge 9 are raised respectively in relation to the first 2 and the second 4 half-shell, without interfering with the subsequent extraction of the spacer device formed in the mold according to the present invention.

The height of the depth gauges 40 facilitates perfect contact between the first perimeter edge 7 and the second perimeter edge 9 when the mold 100 is in the closed configuration.

In the mold 100, the first perimeter edge 7 and the second perimeter edge 9 respectively constitute the access openings for the at least one insert 15 of the first half-shell 2 and/or for the at least one insert 15 of the second half-shell 4 and/or for the second half-shell 4 itself. Through these access openings, or at least through the access opening determined by the first perimeter edge 7 of the first half-shell 2, it is possible to introduce the material that constitutes the spacer device 1000.

As a result of the mold according to the present invention, the material making up the spacer device 1000 can have a very high viscosity. In fact, the forces involved in the mold 100 closing step, as well as the specific conformation thereof, also facilitate compression of a very dense and/or viscous material, ensuring that the same flows over the entire area consisting of the cavity 6 and the additional cavity 6a, without leaving empty spaces, thereby obtaining a fully formed spacer device 1000.

In particular, in at least one version of the present invention, the material forming the spacer device is intentionally dense and/or viscous and/or manipulable, so as to limit as much as possible the volumetric shrinkage phenomena that occur during the solidification and/or polymerisation step of the material itself, and which are very pronounced in the case, for example, of cement in a liquid state.

This also facilitates the realisation of the forming operations, in the case in which this material is positioned on both the first and second forming surfaces (when the mold is in open e.g. book-like form).

Thanks to the conformation of the mold 100, in fact, when it is closed, an active pressure is created able to compress and deform the material constituting the spacer device, causing it to flow into all the areas of the cavity 6 and/or the additional cavity 6a, so as to obtain a perfect filling of them by the material in question, with consequent optimal forming of the spacer device in all its parts.

The material constituting the spacer device is supplied to the mold by casting and/or placement on the first forming surface 8 and/or the second forming surface 10, but, as mentioned, not by injection into the mold 100.

With regard to FIGS. 14 to 23, reference will now be made to a mold 200 for forming the femoral knee spacer device 2000.

The mold 200 corresponds substantially to that of the preceding embodiment, and thus it will not be further described, unless for those details that are different than the mold 100.

What changes most are the forming surfaces 208 and 210, which in the mold 200 are dedicated to forming the femoral knee spacer device 2000.

Figures 24A, 24B:
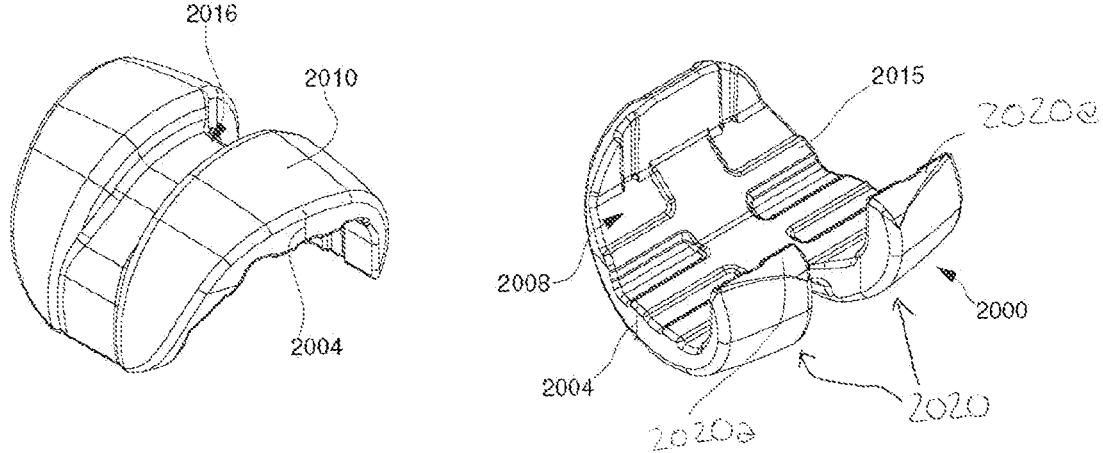
FIGS. 24A and 24B show perspective views respectively from above and from below of a femoral spacer device obtainable with the mold of previous figures.
Figure 25:
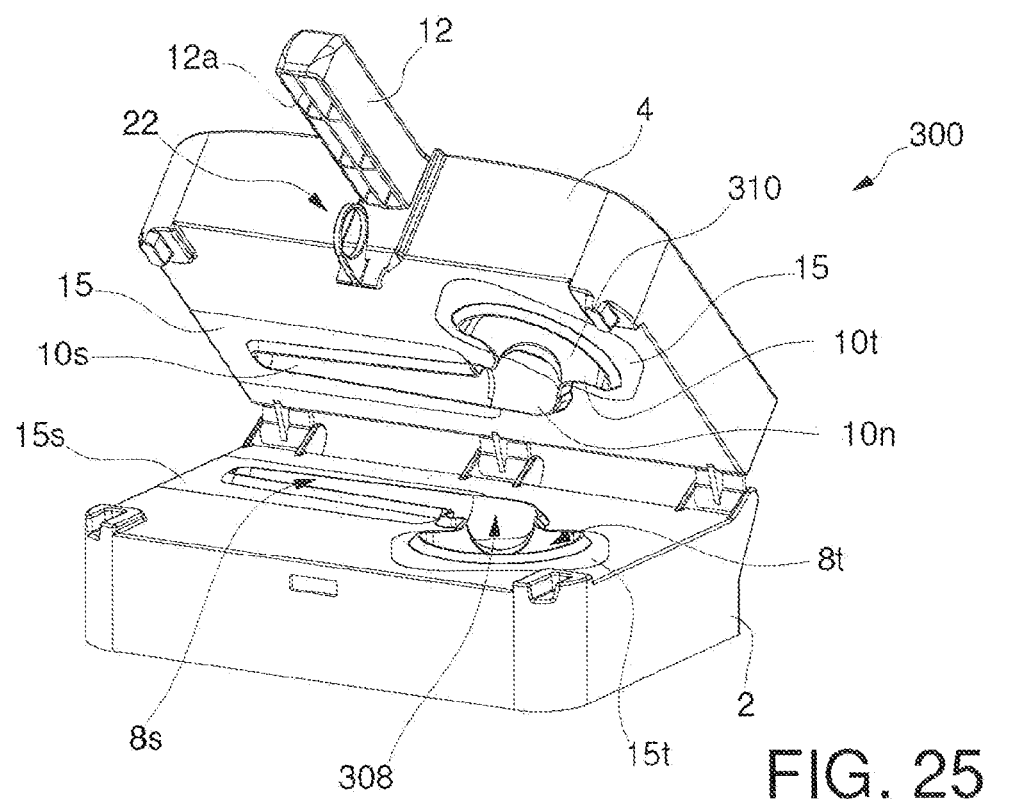
FIG. 25 illustrates a perspective view of a mold for forming a hip spacer device, in a partially open configuration.
Figure 26:
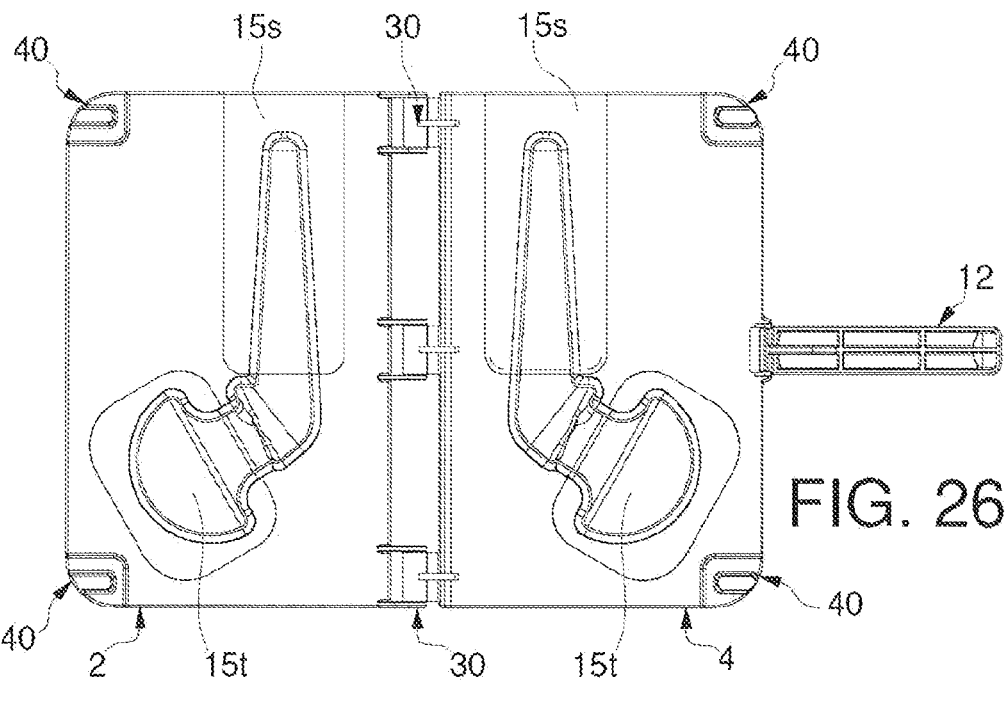
FIG. 26 illustrates a plan view of the mold of FIG. 25, in a completely open configuration.
Figure 27:
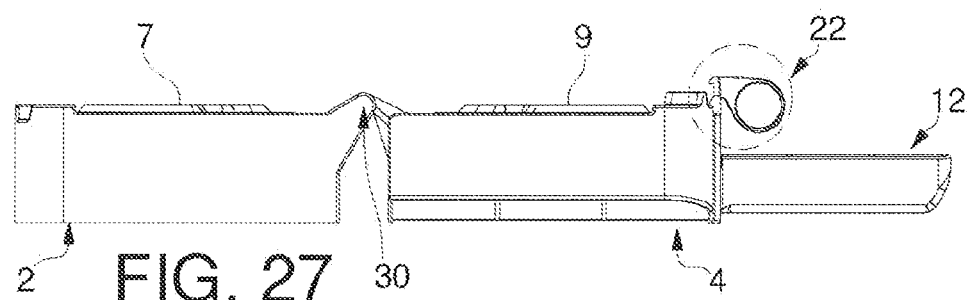
FIG. 27 illustrates a side view of the mold of FIG. 26.

With particular reference to the Figures indicated, the first forming surface 208 is adapted to form the upper face 2008 of the femoral knee spacer device 2000, the latter being illustrated in FIGS. 24A and 24B, while the second forming surface 210 is adapted to form the lower face 2010 of the spacer device 2000.

The lower face 2010 is adapted in use to be articulated with the tibial knee spacer device (for example, the one illustrated in FIGS. 13A and 13B or a generic tibial knee spacer device) or with the tibial end of a knee joint of a patient while the upper face 2008 is adapted in use to be implanted at the end of the femoral bone of the patient at the knee joint.

Both the first forming surface 208 and the second forming surface 210 have a curved profile; in particular, the first forming surface 208 has a convex pattern while the second 210 has a concave pattern.

The femoral spacer device has a substantially rectangular or oval or C-shaped conformation in the plan view and a thickness 2004 given by the distance between the upper face 2008 and the lower face 2010 of the spacer device 2000.

The first forming surface 208 is constituted by a (first) base 208a, convex with respect to the upper face 2a of the first half-shell 2 and/or to the first face 15a of the at least one insert 15 placed in the first half-shell 2, and a (first) side surface 208b. The (first) side surface 208b extends along the perimeter of the (first) base 208a, from the latter to the first perimeter edge 7. The first perimeter edge 207 is therefore raised with respect to the (first) base 208b and/or the upper face 2a and/or to the first face 15a.

In particular, the (first) base 208a may have a series of ribs 15 adapted to determine the formation of respective longitudinal grooves 2015 of the upper face 2008 of the tibial plate 2001.

Furthermore, the first face 15a is connected to the first peripheral edge 7 by means of a (first) raised surface 8c.

The second forming surface 210 consists of a (second) base 210a, concave with respect to the lower face 4a of the second half-shell 4 and/or to the first face 15a of the at least one insert 15 inserted in the second half-shell 4. In one version, the (second) base 210a rises from the first face 15a of the at least one insert and/or from the lower face 4a and the second perimeter edge 9 is therefore raised with respect to said face 15a and/or 4a.

In particular, the (second) base 210a may have a substantially smooth surface, although, in at least one version of the invention, it comprises a longitudinal central rib 216 corresponding to a substantially rectangular base recess 2016 present at the lower face 2010 of the femoral spacer device 2000.

Considering now FIGS. 43A to 51B, reference will be made to a mold 200 for forming a femoral spacer device for knee 2000.

The mold 200 substantially corresponds to that of the previous embodiment, and will therefore not be described further, except for those aspects which differ from the mold 200.

In this version of the mold, the first forming surface 208 of the first half-shell or lower body 2 is the manual application area of the material that will form the spacer device or bone cement. Therefore, in this version, the material or the bone cement for forming the spacer device 2000 is loaded and/or positioned in that surface.

Compared to the previous version of the mold 200, the first forming surface 208 is much more "spacious" as it accommodates substantially all the material or bone cement necessary for the forming of the spacer device 2000. Therefore, the first forming surface 208 is suitable to form, in use—in at least one version—substantially the entire spacer device (meaning in this case the upper face 2008 of the femoral spacer device and substantially its entire thickness).

The second forming surface 210 is therefore only responsible for forming the lower face 2010 of the spacer device 2000.

In this way, it is easier to position the material or cement and also the subsequent extraction of the already formed spacer device.

Figures 20, 21, 22:
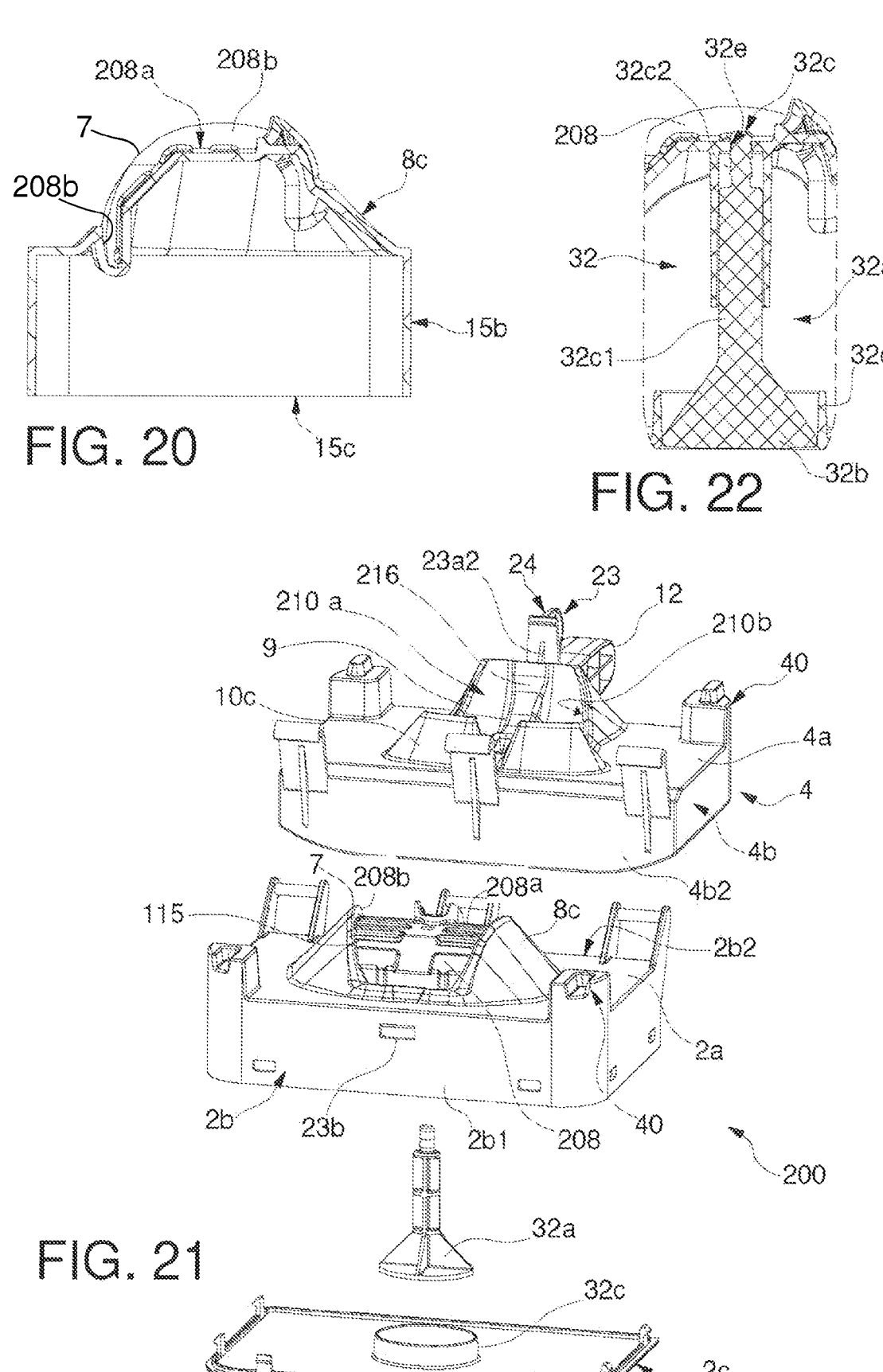
FIG. 20 illustrates a sectional view taken along the plane of trace B-B of the insert of FIG. 19.
FIG. 21 is an exploded view of the mold of FIG. 14.
FIG. 22 is an enlarged detail view of an element of the mold of FIG. 14.
Figure 23:
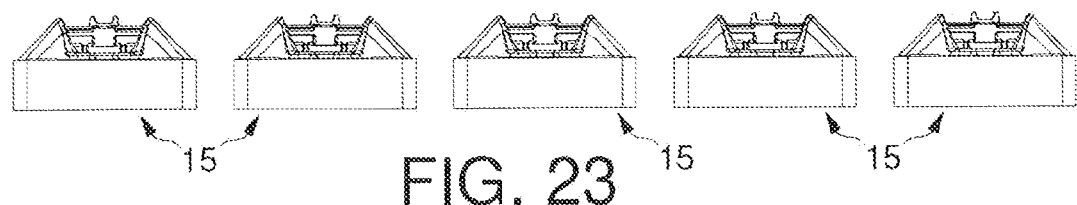
FIG. 23 illustrates a variety of possible inserts of FIG. 19A, having, from left to right, very small (XS), small (S), medium (M), large (L), very large (XL) size respectively.
Figures 49B, 50A:
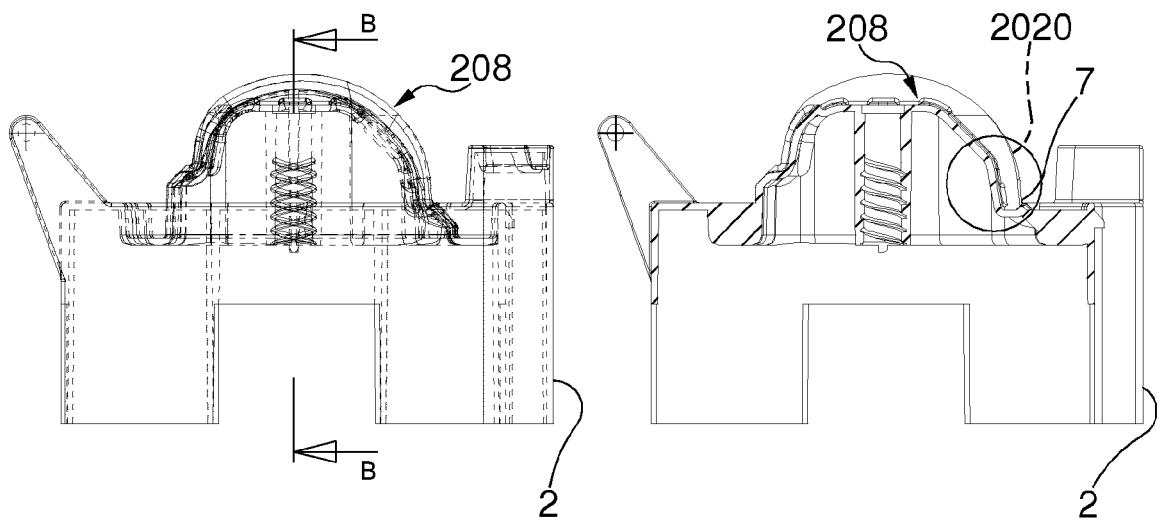
FIG. 49B illustrates a sectional view taken along the plane of trace A-A of FIG. 49A.
FIG. 50A illustrates a side view of the component of FIG. 49A.
Figures 49C, 50B, 51A, 51B:
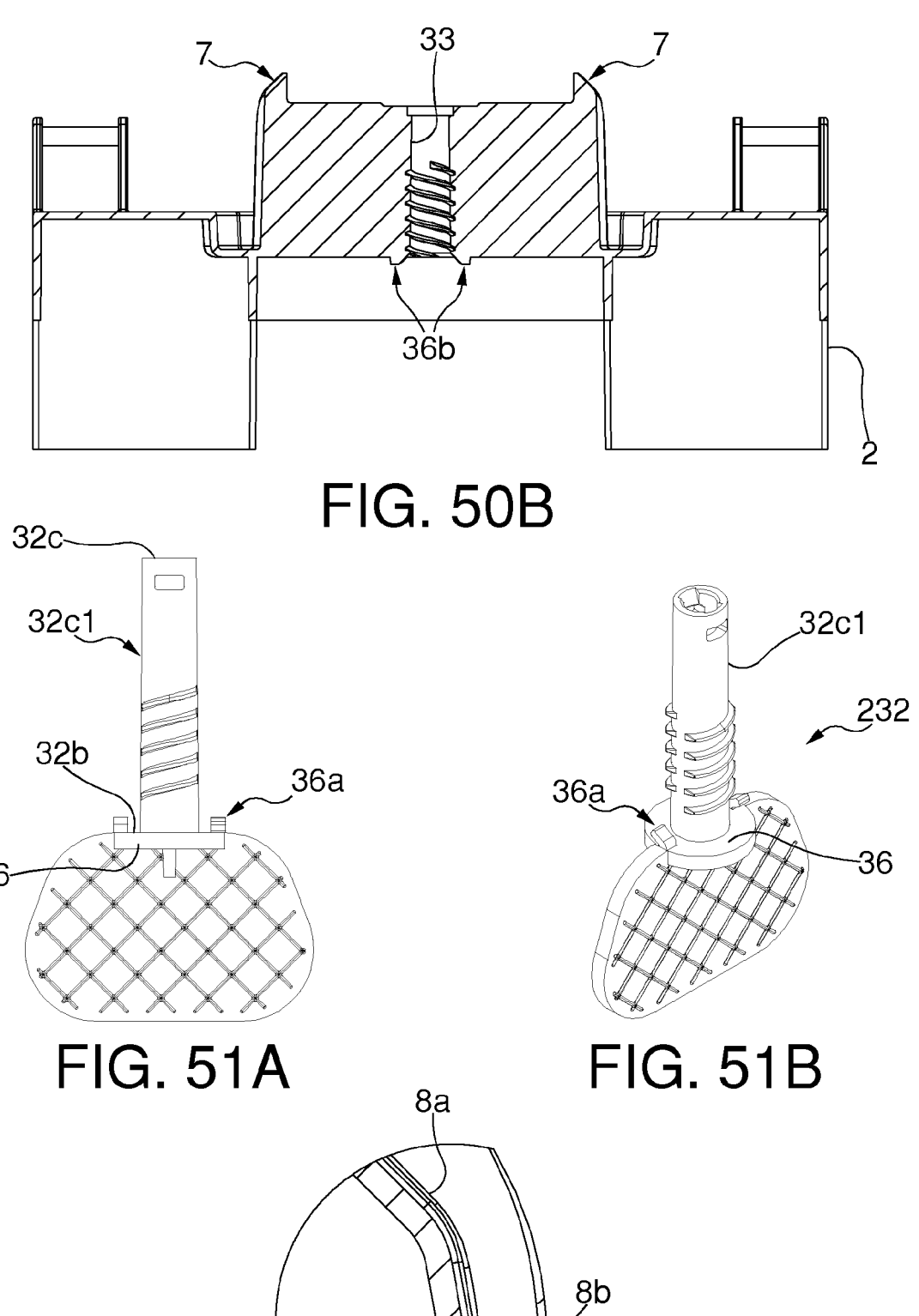
FIG. 49C illustrates an enlarged detail of FIG. 49B.
FIG. 50B illustrates a sectional view taken along the plane of trace B-B of FIG. 50A, FIGS. 51A and 51B respectively show a front and perspective view of an element of the mold of FIG. 43A.

As can be seen, for example, from the comparison between FIG. 20 and FIG. 49C, at the portion of the first forming surface 208 and in proximity of the perimeter edge 7, the lateral surface 208b can have a trend substantially rising towards the cavity 6, for example having a substantially U-shaped conformation (as visible in FIG. 20) or extending outwards in a substantially perpendicular manner with respect to the adjacent base portion 208a (as visible in FIG. 49C).

This portion is placed at the condylar portion 2020 of the knee joint, with reference to the spacer device 2000, and in greater detail with reference to the free ends 2020a of the condylar portion 2020 of the device itself.

In the case of the embodiment illustrated in FIG. 49C, the removal of the molded device may be easier.

In this version of the invention (possibly also applicable to the other versions described), as illustrated for example in the enlarged detail of FIG. 43B, the mold 200 has a removable restraint structure 22 substantially similar to that of the previous versions, comprising hooking means 23 removable, for example snap-on.

The removable coupling means 23 comprise, for example, a tooth or protrusion element 23a, adapted to be engaged in a removable way in a suitable engagement seat 23b, in such case, the tooth is placed at the first half-shell or lower body 2 while the engagement seat 23b is placed for example at the coupling means 23 which are placed at the second half-shell 4.

In this version, the coupling means 23 comprise a suitable bracket 23a1 adapted to carry the engagement seat 23b, of a length such as to be able to bring the engagement seat 23b at the tooth or protrusion element 23a, when the second half-shell 4 is superimposed on the first half-shell 2 to close the mold 200 and thus start the forming step of the spacer device 2000.

A second end or region of the bracket 23a1 carries a trigger element 24a. In this case, the trigger element 24a has a bracket conformation, suitable for example to be gripped by a user or adapted to be engaged by a finger of a user, so as to cause the release of the two half-shells of the mold 200 at the end of forming of the spacer device.

The action on the trigger element 24a determines the release and/or disengagement of the tooth element or protrusion 23a from the engagement seat 23b. Since the trigger element 24a is in proximity to the handle 12, the operator can hold the handle 12 substantially in a single step, release the coupling means 23 by means of the trigger 24a and move the second half-shell 4 away from the first half-shell 2, causing the opening of the mold 200, for example by rotating one with respect to the other, again by means of the handle 12.

On the opposite side with respect to the trigger element 24a, there is the seat 13 for the handle 12.

The trigger element 24a has a substantially bracket and/or rectangular or semicircular or ergonomic shape, suitable for the engagement of at least one finger of the hand of the operator responsible for forming the spacer device, so as to apply a force, for example pulling or pulling away.

There may also be a lid element 60, for example shaped like a rectangle, a square, a polygon, a circular sector or a circle.

The lid element 60 is able to be housed in a corresponding seat present in the upper face 4c of the second half-shell 4.

The lid element 60 is designed to allow the positioning of the user's hand, for example resting on it, for example during the closing and/or opening phases of the mold 200.

The details of this version can also be applied to other versions described here, without departing from the scope of protection of the present invention.

With particular reference to FIGS. 25 to 29, which illustrate a mold 300 for forming a hip spacer device (the latter illustrated in FIGS. 30A, 30B and 30C), or with particular reference to FIGS. 31 to 35, which illustrate a mold 400 for forming a shoulder spacer device (the latter illustrated in FIGS. 36A and 36B), it will be noted that, in such molds, there are respectively a first half-shell 2, a half-shell 4 and at least one insert 15.

In particular, the at least one insert 15 comprises a first forming surface 308, 408, which determines the forming of a first longitudinal half of an articular spacer device for the hip or shoulder, and a second forming surface 310, 410, which determines the forming of a second longitudinal half of this spacer device. Therefore, the first and second longitudinal halves of the spacer device include both surfaces in contact with the patient's bone and joint surfaces.

Unless the contrary is expressly indicated, the characteristics and elements described for the previous embodiments may be present and provide the same results also for the molds 300 and 400 to which reference will now be made.

In particular, the first half-shell 2 and/or the second half-shell 4 can comprise at least a first insert 15 which comprises the entire first forming surface 308, 408 and the entire second forming surface 310, 410.

In this way, similarly to what has been described for the first embodiment of the mold 100 and for the second embodiment of the mold 200, each insert 15 has a certain size or dimension, for a corresponding size or dimension of the respective spacer device which is format.

The interchangeable inserts 15 may comprise a series of first inserts or stem inserts 15s and/or a series of second inserts or head inserts 15t. In this way, each size of the forming surface of the stem portion can be variously coupled with one or each size of the forming surface of the head portion and vice versa.

Furthermore, it is possible that only the stem insert 15s or only the head insert 15t is provided in the mold, thus being able to vary the size of only that portion of the spacer device corresponding to the insert.

In the version illustrated in the figures, a first insert 15s and a second insert 15t can be present for each half-shell.

The first insert 15s is an insert for forming the stem portion 3006, 4006 while the second insert 15t is an insert for forming the head portion 3002, 4002 of the hip spacer device 3000 or shoulder 4000.

Figure 35:
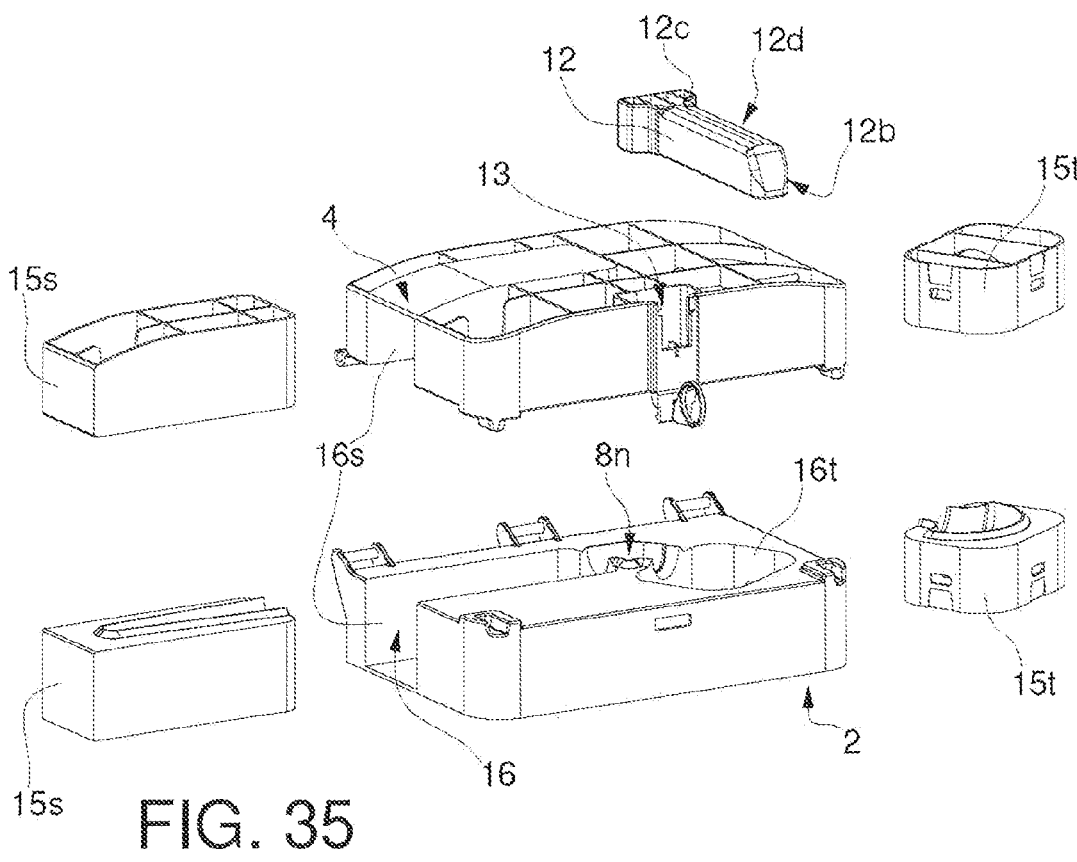
FIG. 35 is an exploded view of the mold of FIG. 31.
Figures 36A, 36B:
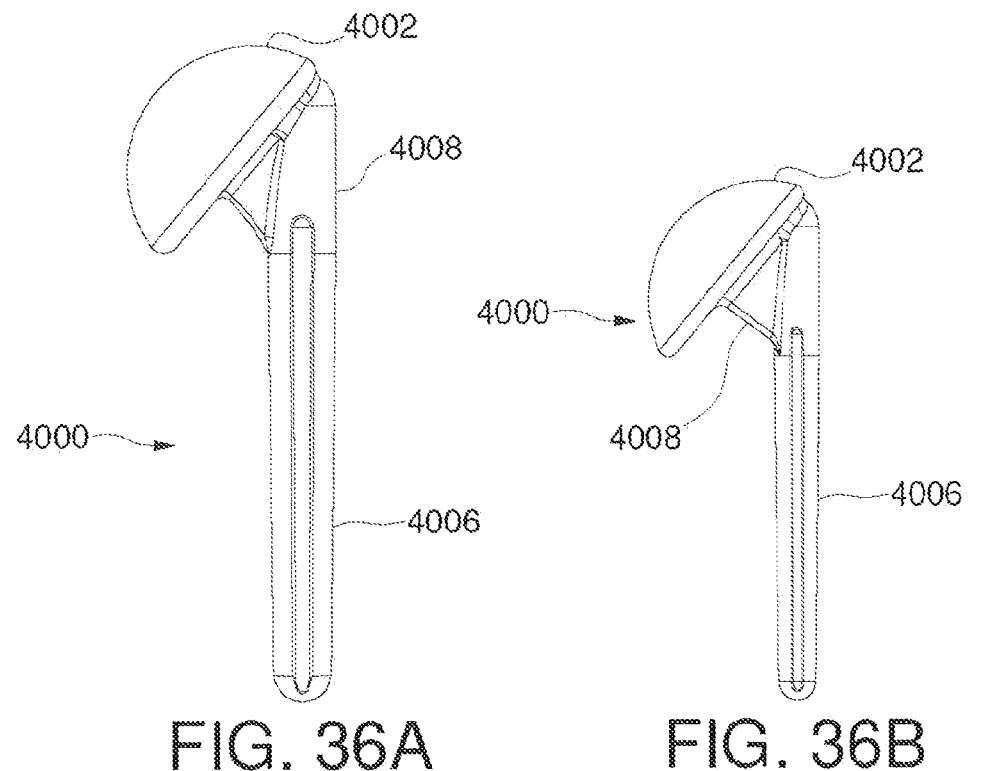
FIGS. 36A and 36B illustrate side views of two examples of shoulder spacer devices (one with a long stem and one with a short stem) obtainable with the mold of the previous FIGS. 31 to 35, FIGS. 37 and 38 respectively represent a plan view and an enlarged detail in section taken along the plane of trace A-A of FIG. 37 of a further version of a mold for forming a tibial spacer device for the knee, FIGS. 39 and 40 respectively represent a plan view and an enlarged detail in section taken along the plane of trace A-A of FIG. 39 of a further version of a mold for forming a femoral spacer device for the knee, FIGS. 41 and 42 respectively represent a plan view and an enlarged detail in section taken along the plane of trace A-A of FIG. 41 of a further version of a mold for forming a hip or shoulder spacer device.

Therefore, as visible for example in FIG. 35, the housing seat 16 includes at least a first seat 16s for the insertion of the first insert 15s and at least a second seat 16t for the insertion of the second insert 15t.

Similarly, the first forming surface 308, 408 of the at least one insert 15 present in the first half-shell 2 comprises at least a first forming surface of the stem 8s and a first forming surface of the head 8t.

Similarly, for the at least one insert 15 present in the second half shell 4, the second forming surface 310, 410 of the at least one insert 15 comprises at least a second forming surface of the stem 10s and a second forming surface of the head 10t.

When the at least one insert is present both in the first half-shell 2 and in the second half-shell 4 of the mold 300, 400, the first forming surface 308, 408 determines the molding of one half of the spacer device 3000, 4000 while the second forming surface 310, 410 causes the molding of the other half of the spacer device 3000, 4000. These halves are specular and symmetrical.

Both the forming surface for the stem 8s, 10s, and the forming surface for the head 8t, 10t, have a substantially hollowed and/or concave base.

The forming surface for the stem 8s, 10s has an elongated course, possibly tapered towards the distal end with respect to the forming surface for the head 8t, 10t.

The forming surface for the head 8t, 10t, on the other hand, has a substantially hemispherical or quarter-sphere conformation, depending on whether the head 3002, 4002 itself has a substantially spherical or hemispherical conformation.

There may then be a portion 8n in the first half-shell 2 and a portion 10n in the second half-shell 4 for forming the neck 3008, 4008 of the spacer device. The neck 3008, 4008 of the spacer device is that area of the spacer device which connects the stem 3006, 4006 to the head 3002, 4002 of the spacer device 3000.

The forming surface of the portions 8n, 10n is concave, with respect to the plane of the faces 2a, 4a of the first half-shell 2 and/or the second half-shell 4 and/or the first face of at least one insert 15.

The portions 8n and 10n act as connecting portions between the first insert 15s and the second insert 15t. Therefore, their forming surface is joined and/or connected to the first forming surface and/or to the second forming surface, respectively present in the first insert 15s and/or in the second insert 15t.

This portion 8n, 10n can be directly part of the first half-shell 2 and/or of the second half-shell 4 (and in this case it is made in one piece with the first half-shell 2 and/or with the second half-shell 4) or it can be carried by a respective further insert (not shown in the figures).

When in use, the first insert 15s and the second insert 15t determine, possibly with the portion 8n, 10n for the neck, the forming surface 308, 408, 310, 410. Also the portion 8n, 10n for the neck, in fact, as said, it has an area of the forming surface 308, 310, 408, 410 corresponding (in negative) to the neck 3008, 4008 itself of the spacer device.

For example, the portion 8n and/or the portion 10n respectively have a forming surface corresponding each to a longitudinal half of the neck 3008, 4008 of the spacer device to be formed.

Similarly, these components determine the cavity 6.

In particular, the portion 8n, 10n is in fluid communication with the first insert 15s and/or the second insert 15t. the portion 8n, 10n, therefore, can have an opening (for example corresponding to one half of the neck section of the spacer device in those areas of junction with the stem (for example formed by the first insert 15s) and with the head (for example formed by the second insert 15t) This opening can be present in a corresponding way, in shape and/or position, on the first insert 15s and/or on the second insert 15t.

When the portion 8n is present, or in any case when the insert 15t and/or 15s are present, although the inserts can be varied according to the selected size of the spacer device to be obtained, there will still be a perfect correspondence between the forming surface 8t, 8s, 8n (for example in particular at their edge or perimetric areas) so as to provide a spacer device with the desired shape.

This means that, if the portion 8n is present and is made as a monobloc with the first half-shell 2 (and/or of the second half-shell 4), the inserts 15t and/or 15s will always have the same size in an area of junction with the portion 8n, regardless of the size of the forming surface carried by the inserts themselves.

If, on the other hand, the 8n portion is present in an insert, it could also have a certain size, which can be combined with the various sizes (or at least with some of them) of the 15t and 15s inserts.

In this way, the forming surface will have no undesired recesses, undercuts and/or steps, and the first perimeter edge 7 and/or the second perimeter edge 9 will be continuous and uninterrupted, despite being present and defined by the insert 15s and/or 15t and/or the portion 8n, 10n, so as to be therefore perfectly corresponding to the shape and desired size of the resulting spacer device.

Therefore, no discontinuities are created in the forming surface 308, 310, 408, 410 as the latter is substantially continuous, although formed by more than one insert or by an insert and by an area of the first or second half shell.

In a completely analogous way, the first perimetric edge 7 and the second perimetric edge 9 are continuous and do not present discontinuities, although they are determined by several inserts or by an insert and by an area of the first or second half-shell.

The correspondence of the at least one insert 15 in its seat 16 is made to measure, since when the at least one insert is inserted, no spaces or cracks are created which could be invaded by the material that constitutes the spacer device 3000, 4000 during its forming phase.

In this way, it is possible to choose for each portion of the spacer device 3000, 4000 the measure or size that best meets the real anatomical and implant needs for the patient.

Each insert 15s, 15t has an overall conformation like that described for the previous embodiments.

Each portion of the first forming surface 308, 408 is adapted to abut against and at the respective portion in the second forming surface 310, 410. It is enclosed between the first forming surface 308, 408 and the second forming surface 310, 410 a cavity 6.

Therefore, the first insert 15s, the second insert 15t and the 8n portion of the first half-shell 2 are connected to each other in fluid communication; same situation for the inserts 15s, 15t and the portion 10n of the second half-shell 4.

The stem 3001, 4001 of the hip and shoulder spacer device may have different lengths, as illustrated for example in FIGS. 30A, 30B, 30C and 36A and 36B respectively. The length, the thickness, the conformation, the section are all parameters that are determined by the type, size and/or size of the at least one 15s insert that is selected for forming the respective portion.

Similarly, the head portion 3002 has a conformation, a size and/or a size that are determined by the type, size and/or size of the at least one insert 15t that is selected for forming the respective portion.

In particular, in at least one version of the invention, the first half-shell 2 and the second half-shell 4 each determine one half of the head portion, taken along the longitudinal trace plane, that is, it passes through the largest dimension of the spacer device itself and which cuts the spacer device 3000, 4000 into two equal and symmetrical halves.

Therefore, in this version, the first half-shell 2 and the second half-shell 4 and/or the at least one insert 15 are symmetrical with respect to an axis of union of the first half-shell and/or the second half-shell or with respect to a plane parallel to the upper face of the first half-shell and/or to the lower face of the second half-shell.

In this case, the articulation surface of the resulting spacer device is also "cut" by the opening plane of the molds. This means that the head insert 15*t*, or rather the first or second perimeter edge 7, 9, also passes through the articulation surface of the head 3002, 4002 of the spacer device 3000, 4000, in at least one version of the invention.

Figures 28, 29, 31:
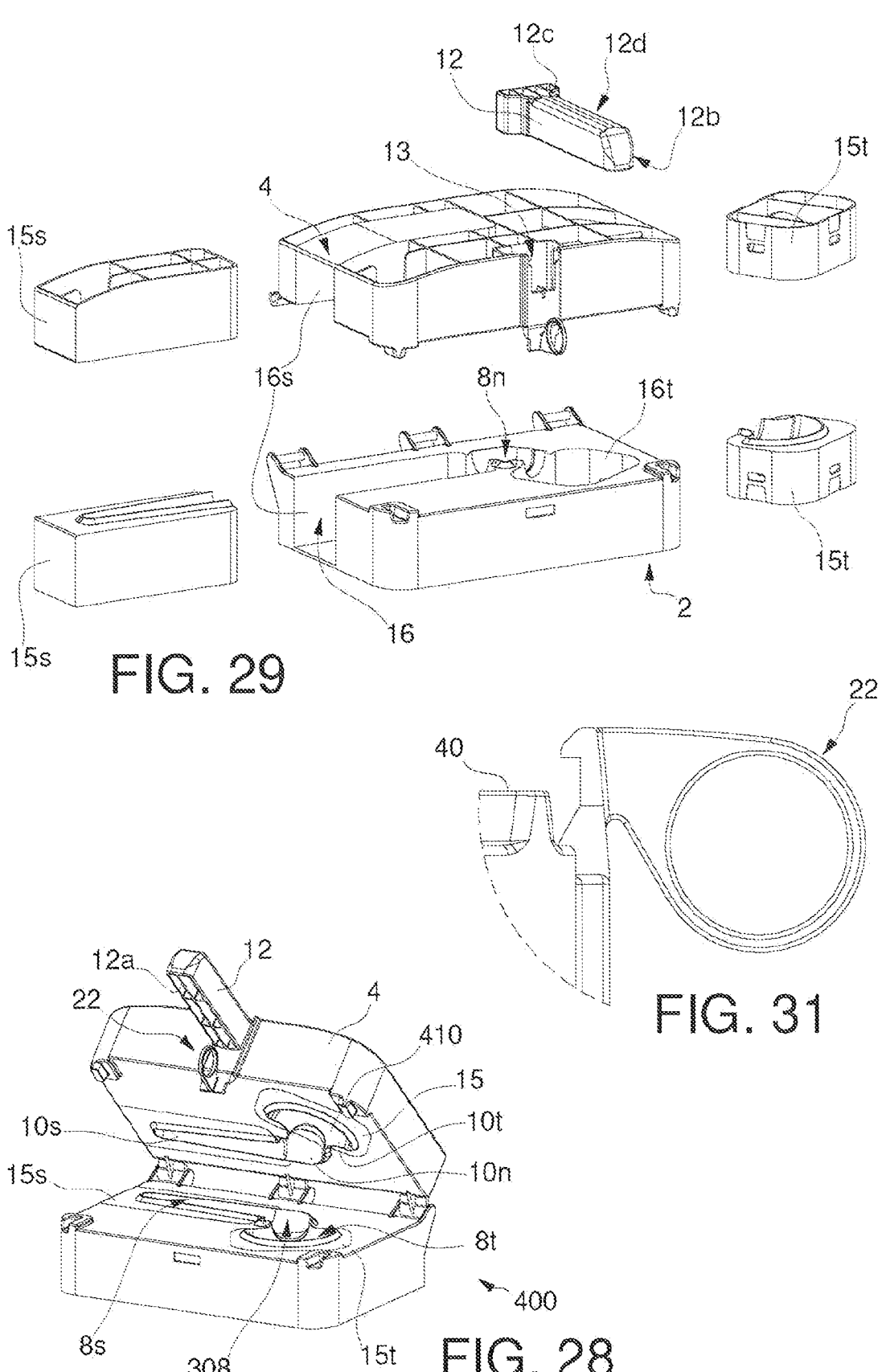
FIG. 28 is an enlarged detail view of an element of the mold of FIG. 25.
FIG. 29 is an exploded view of the mold of FIG. 25.
FIG. 31 illustrates a perspective view of a mold for forming a shoulder spacer device, in a partially open configuration.
Figure 32:
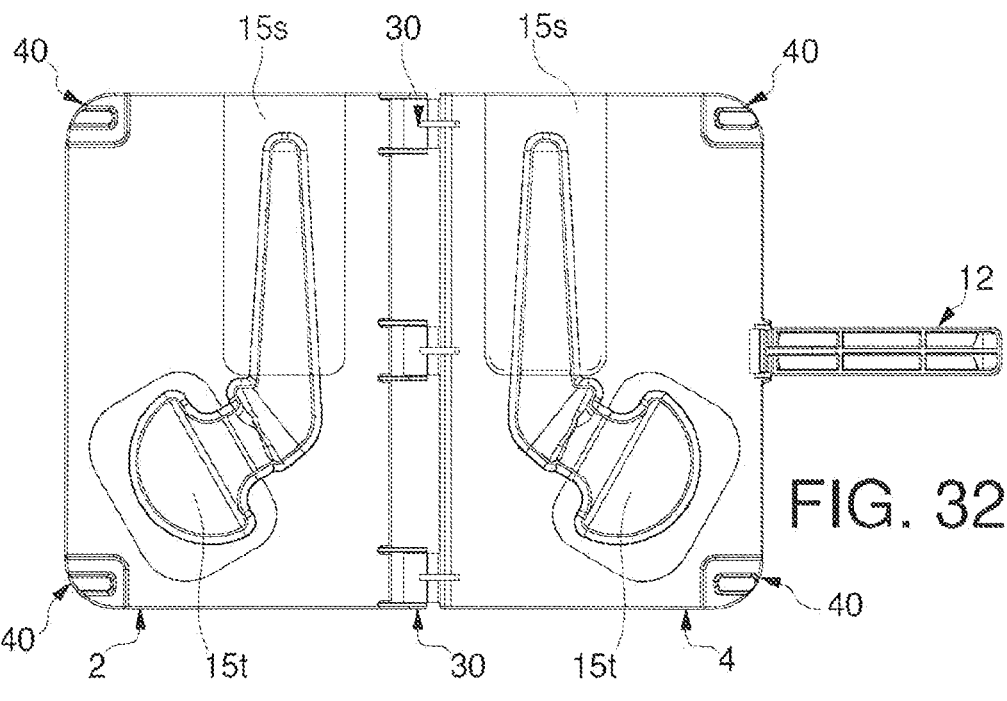
FIG. 32 illustrates a plan view of the mold of FIG. 31, in a completely open configuration.
Figure 33:
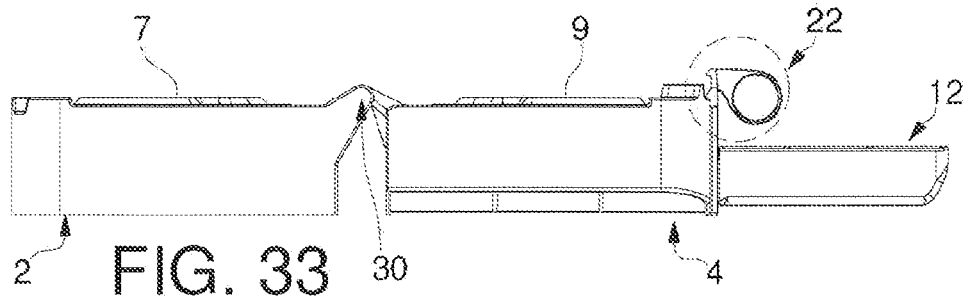
FIG. 33 illustrates a side view of the mold of FIG. 32.
Figure 34:
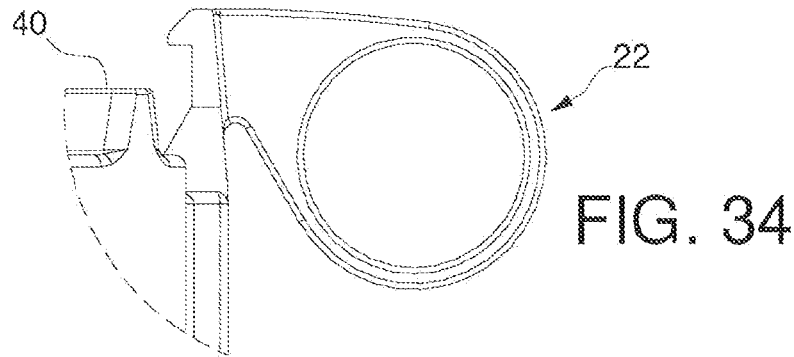
FIG. 34 is an enlarged detail view of an element of the mold of FIG. 25.

As can be seen, for example, in FIG. 29 for the mold 300 and in FIG. 35 for the mold 400, but also applicable to the previously described molds 100 and 200, the handle 12 can comprise a first end 12*b*, distal from the second half-shell 4 and a second end 12*c*, proximal to the second half-shell 4, as well as an elongated body 12*d*, which extends from the first end 12*b* to the second end 12*c*. When this handle is removable, the second end 12*c* has a conformation corresponding to that of a suitable housing seat 13. The housing seat 13 is arranged in the second half-shell 4, for example at its upper face 4*c*.

Figures 46A, 46B, 47A, 48:
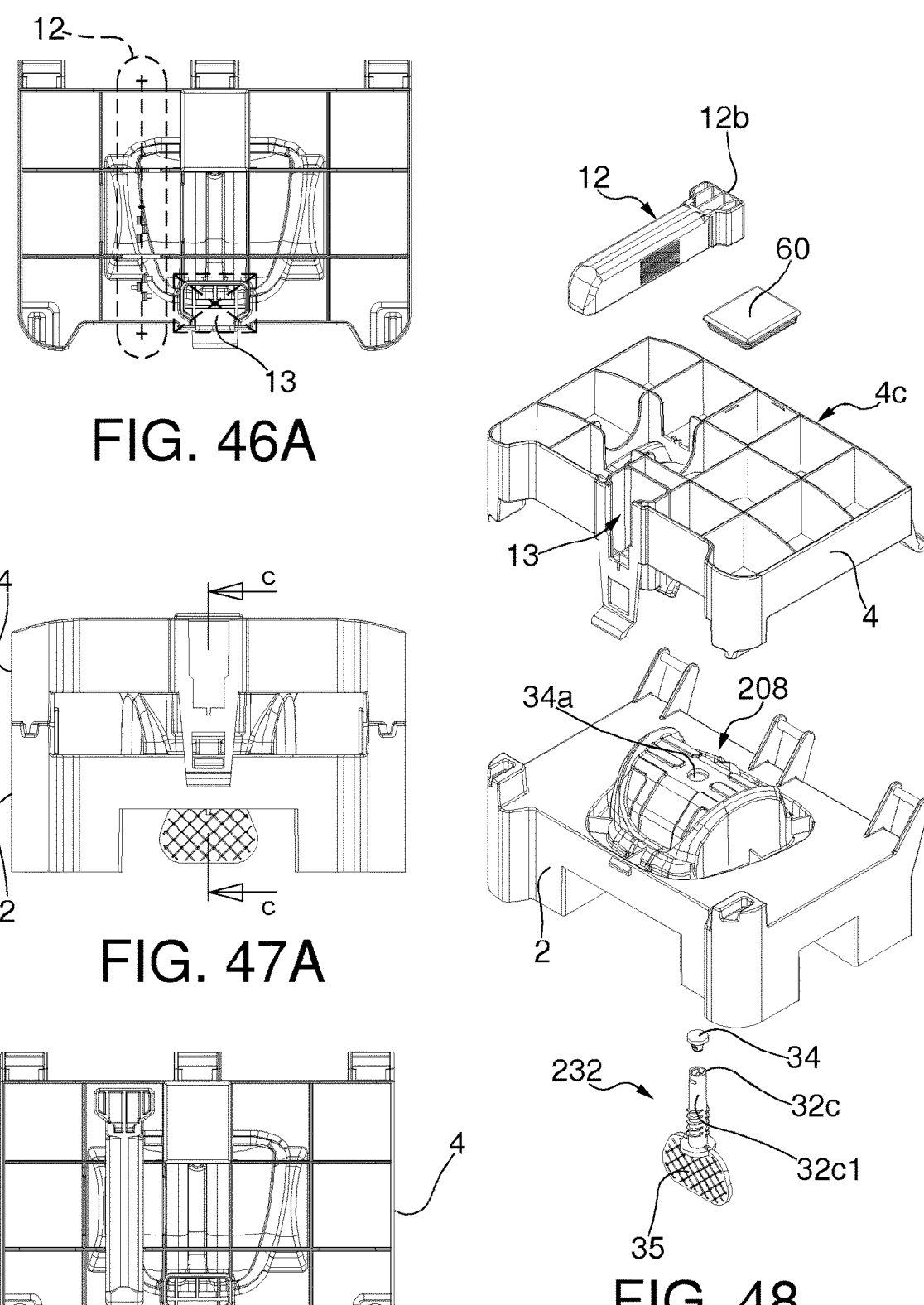
FIG. 47A illustrates a front view of the mold of FIG. 43A.
FIG. 48 illustrates an exploded view of the mold of FIG. 43A.
Figure 49A:
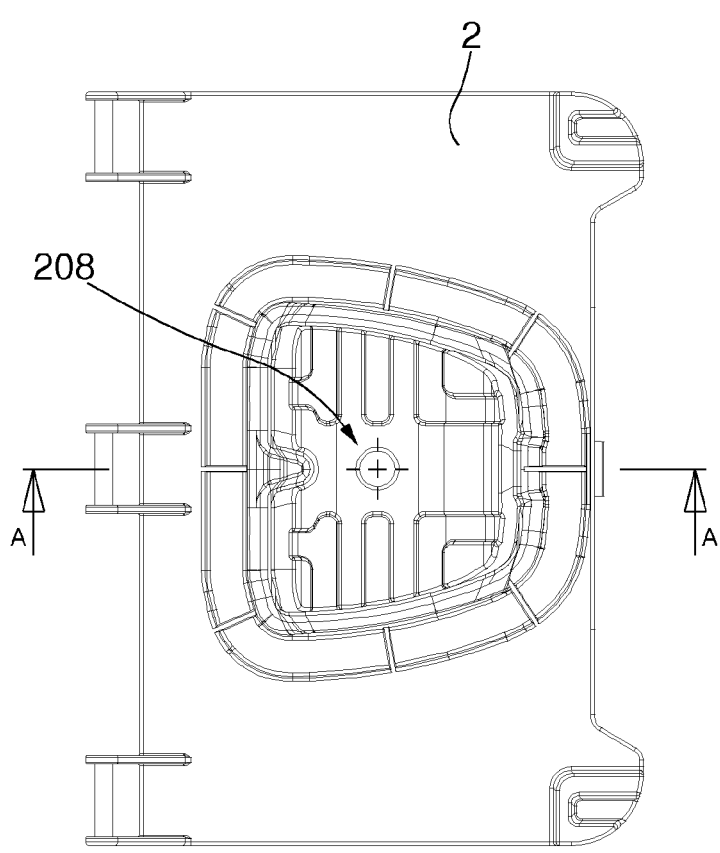
FIG. 49A illustrates a plan view of a component of the mold of FIG. 43A.

In at least one version of the invention, the second end 12*c* has a width and/or a thickness greater than the width and thickness of the elongated body 12*d*. Furthermore, the second end 12*c* can have a width and/or a thickness greater than the width and thickness of the first end 12*b*. Similarly, the housing seat 13 will have a width and/or thickness corresponding to that of the second end 12*c*. Thanks to the insertion of the second end 12*c* into the housing seat 13, the handle 12 will move into position, so that the operator responsible for forming the spacer device can act on it, and therefore apply the necessary force, to close the mold 100, 200, 300, 400 bringing the first half-shell 2 and the second half-shell 4 abutting together, equipped with at least one insert 15, and therefore the first peripheral edge 7 on the second peripheral edge 9. Thanks to this expedient of the handle 12, when the mold is not in use its overall dimensions are considerably reduced, with positive repercussions also on the dimensions of its packaging and for its storage and transport. FIGS. 46B and 46A show respectively the position of the handle 12 when not in use (in FIG. 46A the transport position of the handle is shown with a dashed line and in FIG. 46B the handle 12 is shown positioned in this transport position).

The spacer device according to the present invention, with particular reference to the hip 3000 and shoulder 4000 devices, but also desirable for the tibial 1000 and/or femoral 2000 knee devices, may comprise at least one inner core, in metallic material, for example. The function of this internal core is to strengthen the structure of the spacer device and thus enable it to withstand more intense loads or stresses during its use.

When present, said inner core is positioned at the first and/or the second forming surface. It can be held in position, for example, by the application of special supports or spacers, for example in the form of a yoke, which, at the end of the forming phase, allow it to be in a substantially central internal position within the spacer device. These supports or spacers can be made of the same material of which the spacer device will be made (but already polymerised and/or solidified), so as to join intimately with that material when molding is completed.

Again, the first and/or second forming surface comprises a finish such that the resulting spacer device has a smooth surface, almost glossy, for example, free of imperfections or molding burrs, substantially free of roughness and irregularities. In this way, the forming step of the spacer device can be unique in the sense that a subsequent polishing step of the resulting spacer device is not necessary. As already mentioned, excesses of material emerge from the first and second perimeter edges during the closing step of the first half-shell and the second half-shell and are cut from these edges so as to form an already finished spacer device, with no visible demarcation lines between the areas formed by the first half-shell with respect to the areas formed by the second half-shell.

As noted above, the mold according to the present invention solves the above-mentioned drawbacks in that it has a solid structure, possibly with a simple hinge, possibly with inserts that can be combined to obtain different versions of the molded spacer device, in which the perimeter edges of the abutment and/or junction of the two half-shells have a sharp-edged joint, as a result of which the forming and/or molding operation is of a simplicity never achieved with the molds of the known type.

In at least one version of the invention, the first perimeter edge 7 and the second perimeter edge 9 have a circular and/or annular and closed pattern.

In fact, the first forming surface 8 and the second forming surface 10 are respectively two surfaces which, although having a conformation corresponding to that of the spacer device to be formed and being carried by at least one insert 15, are surfaces enclosed by the first perimeter edge 7 and from the second perimeter edge 9 which are substantially continuous along their entire perimeter for the reasons described above.

It has been seen how the molds according to the present invention can have a plurality of interchangeable inserts, selectable on the basis of the size and/or conformation of the spacer device to be formed or of a part thereof.

The forming surface of each insert, therefore, has a different length and/or thickness and/or width and/or size, from insert to insert, in order to allow this modularity and variety of the spacer device to be formed.

For this reason, the present invention also refers to a kit for a mold as described above.

Furthermore, it is possible that in one version of the invention, the same mold, equipped with a first half-shell and a second half-shell, has at least one seat for housing an insert, the latter comprising a forming surface which, at depending on the choice of the surgeon and the contingent need, it corresponds to that of a knee, hip or shoulder tibial or femoral spacer device. In this way, therefore, a single mold, with its possible hinge means, centering, handle, etc., can form any type of spacer device, depending on the insert that is chosen and is housed in the respective seat.

Therefore, when the extractor means are present, they will be positioned, in this version, at at least one insert, so as to make the latter disposable, while the first and second half-shells will remain intact for subsequent uses.

Furthermore, in a further variant of the present invention, in order to ensure perfect adhesion between the insert and the seat for its housing, means for permanent attachment and/or connection between the insert and the seat for its housing can be provided. In this way, after the surgeon has selected the correct insert, based on the implant needs, and inserted it in the appropriate seat of the mold, a permanent bond will be created between the insert and the mold so that it will no longer be possible to extract the insert from the latter.

The permanent hooking and/or connection means can be suitable gluing and/or adhesive means and/or mechanical connection means of an unsolvable type.

In an alternate version, such means are not present.

A further advantage conferred by the present invention, and in particular by the conformation of the first forming surface and/or of the second forming surface and/or of the cavity, is linked to the fact that it is sufficient to insert the material to be molded in a single step or operation. as the active pressure that is developed with the closure of the mold allows the material itself to flow and occupy the entire molding cavity itself. This is also possible in the presence of at least one insert, as the latter still creates a fluidic continuity between the various parts of the cavity, although these are formed by different inserts or by at least one insert and a portion of the mold. In this sense, it is not necessary to fill with material and/or mold first a portion of the spacer device and then another part of it: the whole spacer device is formed in a single forming step thanks to the mold according to the present invention.

Thanks to the mold according to the present invention, moreover, it is possible to guarantee a substantially hermetic and constant closure for the entire hardening and/or polymerization time of the material constituting the spacer device.

The rigidity of the molds according to the present invention, and of their possible inserts, also guarantees the non-deformability of the mold and therefore the correct molding of the relative spacer device.

According to a further version illustrated in FIGS. 37 to 42, the at least one insert 15 may comprise at least one channel 150. Said channel 150 is positioned adjacent to at least one between the first perimeter edge 7 and the second perimeter edge 9 and/or at least one between the first forming surface 8, 208, 308, 408 and the second forming surface 10, 210, 310, 410.

The term "adjacent" means that the channel 150 departs directly from the first or second perimeter edge or is of some distance, albeit small, from that perimeter edge. The same applies to the first or the second forming surface.

Figures 37, 38, 39, 40, 41, 42:
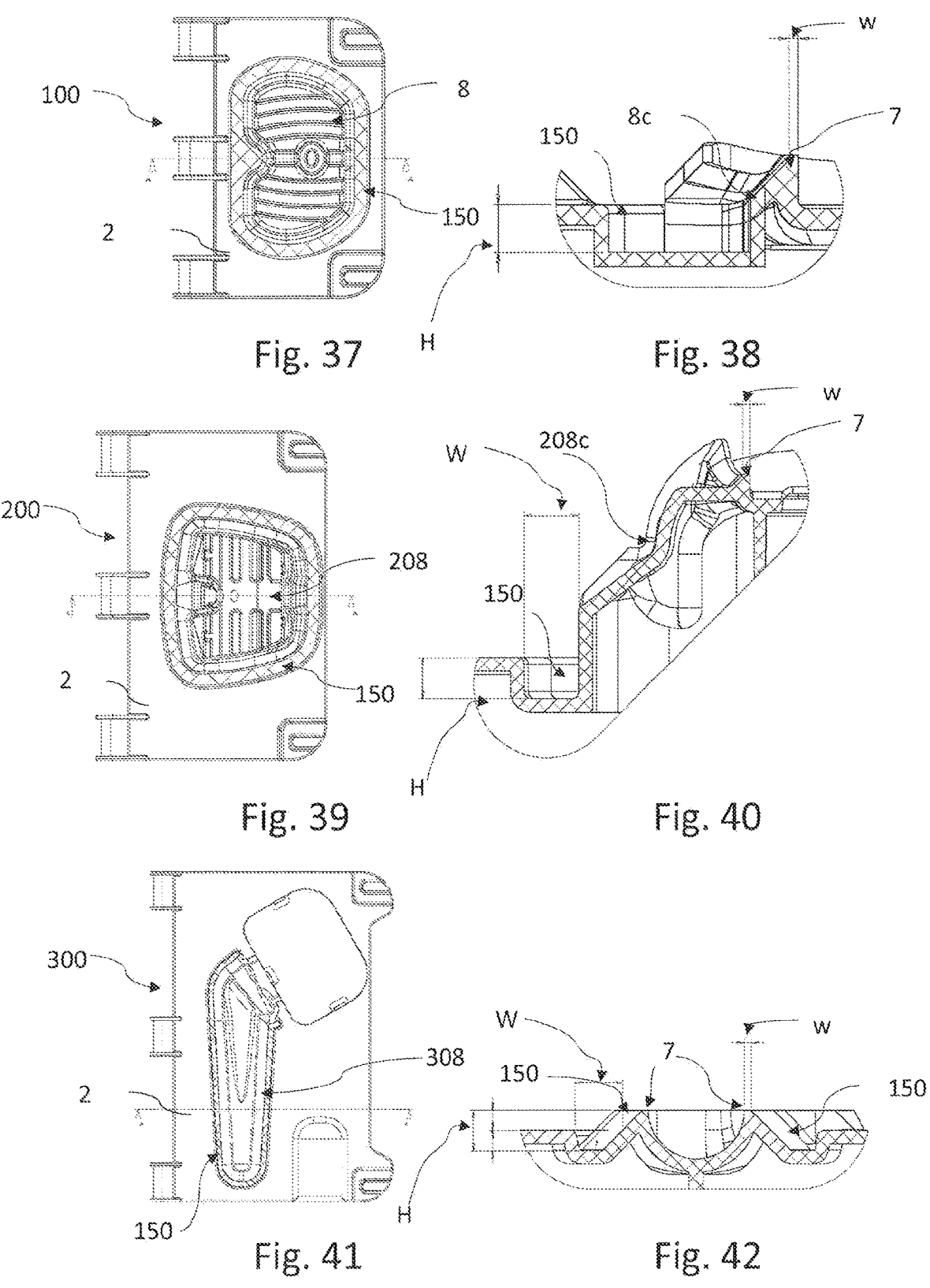

For example, as can be seen in FIGS. 38 and 40, the channel 150 departs from the (first) raised wall 8c, 208c.

This channel 150 is a kind of gutter. Its function, indeed, is to receive in use the excess material forming the spacer device.

The channel 150 has a trend corresponding substantially to that of the first perimeter edge 7 and/or the second perimeter edge 9 and/or the first and/or the second forming surface and/or a part thereof.

According to one version, the channel 150 is positioned only at the first half-shell or lower body 2.

According to a further version especially dedicated to the mold for forming a hip or shoulder spacer device, the channel 150 can only be positioned at the at least one stem insert.

If necessary, the channel 150 may also be placed adjacent to or along the first connecting portion and/or the second connecting portion.

Alternatively, for the mold for forming a hip or shoulder spacer device too, the channel 150 may also be placed at (adjacent to and/or along) the entire forming surface.

As mentioned above, this channel 150 is adapted to collect the excess cement or in any case the excess material used for forming the spacer device. In this version, indeed, during closure of the mold the excess material exits or overflows from the cavity formed by the first and second forming surfaces and flows or drips into this channel 150, where it continues normal polymerisation.

Furthermore, the channel 150 may have a surface, at least at the bottom, which is knurled and/or has a certain roughness or texture or finish.

In this way, said surface which is knurled and/or has a certain roughness or texture or finish, determines strong adhesion to the cement or to the excess material that flows into it after polymerisation.

In this way, when the mold opens, the channel 150 and/or its adhesion to the cement or excess material aids in the detachment of the excess material flowing precisely into the channel, thereby separating the resulting spacer device both from such excess material and from the forming surface itself.

In this way, too, the spacer device obtained is free of molding burrs, which remain attached to the mold and in particular to the channel 150.

The channel 150 thus acts almost like a "trap" for the excess material.

As can be seen from the accompanying Figures, the channel 150 has a cavity in recess with respect to the surface of the first half-shell and/or the second half-shell, with a wall substantially perpendicular or inclined with respect to the latter.

From a dimensional point of view, the channel 150 can have a width W of about 8 mm or between 6 mm and 10 mm and/or a height or depth H of about 5 mm or 6 mm or between 4 mm and 8 mm.

As can be seen, for example in FIG. 38, the height H of the channel 150 may be given by a first section and a second section, wherein the first section is formed by the distance between the upper face of the first half-shell and the deepest point of the channel, while the second section is given by the distance between the upper face of the first half-shell and the outermost or highest point of the channel 150. In one version of the invention, the first and the second section are of the same size, for example about 3 mm.

The outermost or highest point of the channel 150 may be equal to the height (from the upper face of the first half-shell) of the perimeter edge 7. A similar situation may occur if a channel 150 is also present at the second half-shell.

The difference between this version of the invention and previous versions, in which there may have been a space or gap outside the forming cavity and at the first and/or second perimeter edge into which the surplus bone cement could be discharged, is that the channel 150 forms a containment chamber for the excess material in which it is trapped. In addition, its surface (at least the bottom one), which is knurled and/or has a certain roughness or texture or finish, increases the adhesion of said excess material and facilitates its detachment, when hardened and/or polymerised, from the spacer device formed.

Once again, the device formed is substantially smooth and free of machining burrs, and therefore does not require any finishing steps.

In at least one version of the invention, the contact surface between the first perimeter edge and the second perimeter edge has a measurement w of 1 mm or of between 0.5 mm and 2 mm.

As can be seen from the present disclosure, this invention also relates to a method for forming a spacer device for replacing a joint prosthesis comprising the following steps: providing a mold comprising a first half-shell or lower body 2 and a second half-shell or upper body 4, wherein at least one of the first half-shell or lower body 2 and the second half-shell or upper body 4 comprises at least one seat 16 for housing at least one interchangeable and/or removable insert 15, providing the at least one insert 15 which is part of a series of inserts, wherein the at least one insert 15 and/or the mold comprises a first forming surface 8, 208, 308, 408 and/or a second forming surface 10, 210, 310, 410 which define therebetween at least one a cavity 6 corresponding to the external configuration of the spacer device, in which the first forming surface and/or the second forming surface has a certain size and/or shape which is different from the size and/or shape of a first forming surface and/or of a second forming surface of a second insert belonging to the series of inserts 15, selecting the at least one insert 15 so as to select the size and/or shape of the first forming surface and/or of the second forming surface according to the anatomical needs of the patient and/or according to the needs in use of the implant, housing the selected at least one insert 15 in the at least one seat 16, providing a material that constitutes the spacer device and positioning and/or pouring this material into the first forming surface and/or into the second forming surface, coupling the first half-shell or lower body and the second half-shell or upper body, with the at least one insert 15 housed in the at least one seat 16, so as to close the mold and delimit, at the first forming surface and the second forming surface, a cavity 6 corresponding to the external configuration of the spacer device, waiting for a time for polymerization and/or hardening of the material and moulding the spacer device.

During the aforementioned molding step, at least one of the first perimeter edge 7 and the second perimeter edge 9 cuts and/or eliminates any forming burrs caused by the moulding of the spacer device.

In at least one version of the invention, the step of positioning and/or casting the material takes place manually, which is to say, for example, without the use of instruments such as material injection tools.

The coupling step comprises operating a handle 12, for example manually, and/or operating a removable constraining structure 22, present in the second half shell 4 and/or the first half shell 2 and constraining in a removable way the first half shell 2 with the second half shell 4.

The operating step comprises actuating coupling means 23, for example snap-on, of a removable type of the removable constraining structure 22 and/or carrying a tooth or protrusion element 23a present at the second half-shell 4 at a suitable engagement seat 23b, having a conformation corresponding and/or complementary to that of the tooth or protrusion element 23a, realised in the first half-shell 2 or vice-versa and engaging, for example by snapping, the tooth or protrusion element 23a in said engagement seat 23b.

The method further comprises a step of extracting the formed spacer device from the mold and such step comprises pulling the first half-shell 2 and the second half-shell 4 away from each other, releasing the coupling means 23 by disengaging the tooth or protrusion element 23a from the engagement seat 23b, and/or acting on a trigger element 24 and/or on the handle 12 for the step of releasing and moving away and/or actuating unidirectional-type extraction means 32, 232, suitable for extracting the spacer device after it has been formed and making the mold and/or the at least one insert 15 disposable.

Such step can comprise pressing a base 32b of a button element 32a so that a tip or end 32c of a pressing body 32c1 of the button element 32a, or wherein the step of actuating comprises screwing a pressing body 32c1 into a suitable seat 33 realised in the first half-shell 2 such that a tip or end 32c of the pressing body 32c1 that faces into the cavity 6 and/or the additional cavity 6a, pushes the spacer device out of the cavity 6 and/or the additional cavity 6a.

The molds described above are subject to numerous modifications and variations within the scope of protection of the following claims.

The invention claimed is:

1. A mold for forming a spacer device for replacing a joint prosthesis, comprising:
   a first half-shell or lower body; and
   a second half-shell or upper body,
   wherein the first half-shell or lower body and the second half-shell or upper body are configured to be removably coupled, in use, so as to define a closed configuration of the mold, in which at least one of the first half-shell or lower body or the second half-shell or upper body comprises a seat for housing an insert,
   wherein the insert is interchangeable and configured to be housed in the seat,
   wherein the insert comprises a first forming surface and/or a second forming surface,
   wherein the first forming surface and the second forming surface define a cavity therebetween corresponding to an external configuration of the spacer device,
   wherein the seat has a conformation complementary and corresponding to a conformation of the insert, and the seat is a recessed seat in the first half-shell and/or in the second half-shell,
   wherein the first forming surface is delimited by a first perimeter edge and the second forming surface is delimited by a second perimeter edge, the first perimeter edge being configured to abut and come into contact, in use, with the second perimeter edge,
   wherein the first perimeter edge and the second perimeter edge respectively extend along an entire perimeter of the first forming surface and of the second forming surface,
   wherein the cavity is defined by coupling of first perimeter edge with the second perimeter edge, and
   wherein one or both of the first perimeter edge or the second perimeter edge are raised with respect to an upper face of the first half-shell or respectively a lower face of the second half-shell, so as to define an interspace between the upper face of the first half-shell and a lower face of the second half-shell.

2. The mold according to claim 1, wherein the insert is part of a series of inserts, wherein the first forming surface and/or the second forming surface of the insert has a predetermined size and/or shape, the predetermined size and/or shape being different from a size and/or shape of a first forming surface and/or of a second forming surface of a second insert belonging to the series of inserts.

3. The mold according to claim 1, wherein the insert has a box-shaped, polyhedron, parallelepiped, or cylindrical conformation, in which the insert comprises a first face and a second face, the first face and the second face lying on two parallel planes, and a perimeter wall, lateral in use, which extends along a perimeter of the first face and the second face.

4. The mold according to claim 3, wherein the first half-shell and the second half-shell have a box-shaped, polyhedron, parallelepiped, or cylinder conformation, in which the first half-shell comprises the upper face, adapted to house the insert and/or the first forming surface, and a side wall, which extends along a perimeter of the upper face, and in which the second half-shell comprises the lower face, configured to house the insert and/or the second forming surface, and a side wall, which extends along a perimeter of the lower face.

5. The mold according to claim 4, wherein the first forming surface comprises a first base that is recessed in relation to the upper face of the first half-shell and/or in relation to the first face of the insert and/or in relation to the first perimeter edge, and a first lateral surface which extends along a perimeter of the first base, from the first base to the first perimeter edge, and wherein the first lateral surface is perpendicular or inclined towards an outside in relation to the first base.

6. The mold according to claim 4, wherein the second forming surface comprises a second base, in recess in relation to the lower face of the second half-shell and/or in recess with respect to the first face of the insert or to the second perimeter edge, and a second lateral surface which extends along a perimeter of the second base, from the second base to the second perimeter edge, wherein the second lateral surface is perpendicular or inclined towards outwardly in relation to the second base.

7. The mold according to claim 6, wherein the first face of the insert is connected to the first perimeter edge by a first raised wall of the first forming surface, and/or the second face on an opposing insert is connected to the second perimeter edge by a second raised wall, the first and the second raised walls being inclined or perpendicular with respect to the first face or respectively the second face.

8. The mold according to claim 4, wherein the seat is a recessed seat in the upper face of the first half-shell and/or the lower face of the second half-shell.

9. The mold according to claim 3, wherein the cavity, the first forming surface, and/or the second forming surface of the mold has a rectangular, oval, or C shape in plan, corresponding a shape of a tibial and/or femoral knee spacer device to be manufactured in the mold, wherein the mold comprises an additional cavity configured to define a stem of the tibial spacer device, placed at the first face of the insert, wherein the additional cavity and the cavity are contiguous to each other or in fluid connection, or wherein the first forming surface and the second forming surface have a curved profile, the first forming surface having a convex development while the second forming surface having a concave development.

10. The mold according to claim 9, further comprising extraction means of a unidirectional or non-return type, configured to extract the spacer device after a forming thereof, and to make the mold disposable, or the insert, wherein the extraction means comprise a button element equipped with a pressing body, a base configured to be operated for extracting of the spacer device, and a tip or end, wherein the pressing body has a pin or peg shape, wherein the tip or end faces the cavity and/or the additional cavity, or wherein the extraction means comprise the pressing body having a base and a tip or end, wherein the pressing body has a thread configured to engage with a seat equipped with a nut screw and placed at the first half-shell, further comprising a cap or lid configured be housed and/or positioned at the tip and in a seat or opening placed at the first forming surface, or a handle adapted to be gripped by an operator in order to screw the extraction means or comprising a discoidal base having a pair of teeth made of a flexible material, so as to allow a rotation of the extraction means but not to allow unscrewing.

11. The mold according to claim 1, wherein the insert comprises a first insert, for forming a stem portion of a hip or a shoulder spacer device, and/or a second insert or head insert, for forming a head portion of the hip or shoulder spacer device.

12. The mold according to claim 11, wherein the seat comprises a first seat for receiving the first insert and a second seat for receiving the second insert, wherein the first forming surface of the insert comprises a first stem forming surface at the first insert and a first forming surface of the head portion at the second insert, and/or wherein the second forming surface of the insert comprises a second stem forming surface at the first insert and a second forming surface of the head portion at the second insert.

13. The mold according to claim 11, further comprising a first portion in the first half-shell and a second portion in the second half-shell for connecting the first insert and the second insert, the first forming surface and the second forming surface being made from the first and the second portions.

14. The mold according to claim 13, in which at least one of the first or the second portions are made in one piece respectively with the first half-shell or with the second half-shell.

15. The mold according to claim 1, wherein the first perimeter edge abuts against, mates with, or is a mirror image of the second perimeter edge, or wherein the first perimeter edge and the second perimeter edge have an annular, closed, or continuous conformation.

16. The mold according to claim 1, wherein the first perimeter edge and the second perimeter edge have flat abutting surfaces which come into direct contact with each other, wherein the flat abutting surfaces are parallel to a support plane for the mold or both have a same outward or inward inclination with respect to the cavity, wherein the abutting surfaces are both inclined, one outwardly and the other one inwardly, with respect to the cavity, or wherein one of the first or the second perimeter edge has an abutment surface and the other one of the first or the second perimeter edge has an abutment seat shaped as an acceptance or housing area for the abutment surface.

17. The mold according to claim 1, further comprising a removable constraining structure, present in the second half-shell and/or in the first half-shell and configured to removably constrain the first half-shell to the second half-shell, or further comprising a removable constraining structure equipped with coupling means.

18. The mold according to claim 17, wherein the coupling means comprise a tooth or protrusion element present at the second half-shell and configured to removably engage an engagement seat having a conformation corresponding or complementary to a conformation of the tooth or protrusion element provided in the first half-shell, or vice versa.

19. The mold according to claim 17, wherein the removable constraining structure comprises a trigger element, and wherein the trigger element is placed at a handle of the mold.

20. The mold according to 19, wherein the removable constraining structure or the coupling means comprise a bracket configured to carry the tooth or protrusion element or the engagement seat, wherein the bracket has an elongated shape which departs from the second half-shell or from the handle for such a length sufficient to bring the tooth or protrusion element at the engagement seat when the second half-shell is brought into abutment against the first half-shell to close the mold.

21. The mold according to claim 20, wherein the bracket has a first end constrained to the second half-shell or to the handle and a second end, opposite to the first end and further away from the first end in relation to the second half-shell, wherein the bracket has a first face facing, in use, toward the first half-shell or towards an interior of the second half-shell and a second face, opposite to the first face, wherein the tooth or protrusion element or the engagement seat is positioned at the second end or the first face, wherein the removable constraining structure comprises a trigger element, or wherein the trigger element is positioned at the second end, at the second face of the bracket, or at the handle.

22. The mold according to claim 17, further comprising a handle adapted to be gripped for bringing the second half-shell to abut against the first half-shell and to apply a force to compress a material for making the spacer device, wherein the handle is placed at the second half-shell and is removable.

23. The mold according to claim 22, wherein the handle has an elongated configuration with a rectangular longitudinal cross-section, with rounded edges, wherein the handle internally comprises reinforcing ribs, wherein the handle comprises a first end, a second end and an elongated body which extends from the first end to the second end, and wherein the second end has a configuration corresponding to a configuration of a housing seat provided in the second half-shell.

24. The mold according to claim 1, wherein the first perimeter edge is connected to the first face by way of a raised wall which is inclined or perpendicular to the first face.

25. The mold according to claim 1, further comprising a hinge positioned in the first half-shell or in the second half-shell, wherein the hinge allows rotation reciprocal of the second half-shell with respect to the first half-shell and a closure of the mold.

26. The mold according to claim 1, wherein the insert comprises a channel adjacent to the first perimeter edge or the second perimeter edge, or one of the first forming surface or the second forming surface, and wherein the channel is adapted to receive in use excess material during a forming of the spacer device.

27. The mold according to claim 26, wherein the channel has a pattern corresponding to a pattern of the first perimeter edge, of the second perimeter edge, or of the first or the second forming surface, or wherein the channel has a surface, at least at a bottom, knurled, rough, or textured, and wherein the channel has a cavity in recess in relation to surface of the first half-shell or lower body or of the second half-shell or upper body, with a wall substantially perpendicular or inclined with respect to the second half-shell or upper body.

28. A method of forming a spacer device for replacing a joint prosthesis, comprising:

providing a mold according to claim 1;

selecting the insert so as to select the size and/or shape of the first forming surface and/or of the second forming surface based on anatomical needs of a patient and/or based on the predetermined requirements of the spacer device;

housing the insert in the seat;

providing a material for making the spacer device and positioning or pouring the material in the first forming surface and/or in the second forming surface;

coupling the first half-shell or lower body to the second half-shell or upper body, with the insert housed in the seat, so as to close the mold and delimit, at the first forming surface and the second forming surface, the cavity corresponding to the external configuration of the spacer device;

waiting a time for polymerizing or hardening of the material and forming the spacer device.

29. The method according to claim 28, further comprising causing, during the step of forming the spacer device, at least one of a first perimeter edge of the first forming surface or a second perimeter edge of the second forming surface, to cuts or eliminate all forming burrs generated by the coupling of the first half-shell or lower body to the second half-shell or upper body and the forming of the spacer device.

30. The method according to claim 28, wherein the step of coupling comprises operating a handle or a removable constraining structure, present in one or both of the second half-shell and the first half-shell, and removably constraining the first half-shell to the second half-shell.

31. The method according to claim 30, wherein the step of operating step comprises actuating removable coupling means of the removable constraining structure, or wherein the step of actuating the coupling means comprises carrying a tooth or protrusion element, present at the second half-shell at an engagement seat thereof, the engagement seat having a conformation complementary to a conformation of the tooth or protrusion element provided in the first half-shell or vice versa, and engaging the tooth or protrusion element in the engagement seat.

32. The method according to claim 31, further comprising a step of extracting the spacer device from the mold, wherein the step of extracting comprises, moving away from each other the first half-shell and the second half-shell, releasing the coupling means by causing the tooth or protrusion element to exit from the engagement seat or by acting on a trigger element of the removable constraining structure or on the handle, and operating unidirectional or non-return extraction means configured to the spacer device after a forming thereof and for disposing of the mold or the insert, and wherein the step of actuating comprises pressing a base of a button element so that a tip or end of a pressing body of the button element facing the cavity pushes the spacer device out of the cavity, or wherein the step of actuating comprises screwing a pressing body into a receiving seat made in the first half-shell so that a tip or end of the pressing body facing the cavity pushes the spacer device out of the cavity.

33. A kit for a mold for forming a spacer device for replacing a joint prosthesis, comprising:

a first half-shell or lower body;

a second half-shell or upper body, the first half-shell or lower body and the second half-shell or upper body being configured to be removably coupled so as to close the mold, wherein at least one of the first half-shell or lower body or the second half-shell or upper body comprises a seat configured to house a removable insert, the removable insert being one of a series of inserts, wherein the seat has a conformation complementary to a conformation of the insert and is a recessed seat in the first half-shell or in the second half-shell, wherein each insert of the series of inserts comprises a first forming surface and a second forming surface, wherein the first forming surface and the second forming surface of each insert has a predetermined size and shape, wherein the predetermined size and shape are different from a size and shape of a first forming surface or of a second forming surface of a second insert belonging to the series of inserts, and wherein each insert of the series of inserts is configured to be housed in seat, wherein the first forming surface is delimited by a first perimeter edge and the second forming surface is delimited by a second perimeter edge, the first perimeter edge being configured to abut and come into contact, in use, with the second perimeter edge, wherein the first perimeter edge and the second perimeter edge respectively extend along an entire perimeter of the first forming surface and of the second forming surface.

\* \* \* \* \*